(12) United States Patent  
Visveshwara

(10) Patent No.: US 9,597,263 B2  
(45) Date of Patent: Mar. 21, 2017

(54) FLUID AND NUTRITION DELIVERY DEVICE AND METHOD OF USE

(71) Applicant: Nadarasa Visveshwara, Fresno, CA (US)

(72) Inventor: Nadarasa Visveshwara, Fresno, CA (US)

( * ) Notice: Subject to any disclaimer, the term of this patent is extended or adjusted under 35 U.S.C. 154(b) by 0 days.

(21) Appl. No.: 14/216,298

(22) Filed: Mar. 17, 2014

(65) Prior Publication Data

US 2014/0276633 A1  Sep. 18, 2014

Related U.S. Application Data

(60) Provisional application No. 61/799,496, filed on Mar. 15, 2013.

(51) Int. Cl.
*A61J 15/00* (2006.01)

(52) U.S. Cl.
CPC ........ *A61J 15/0003* (2013.01); *A61J 15/0069* (2013.01); *A61J 15/0073* (2013.01); *A61J 15/0092* (2013.01); *A61J 15/0096* (2013.01)

(58) Field of Classification Search
CPC .............. A61M 25/0043; A61M 31/00; A61M 25/0032; A61M 2210/0618;

(Continued)

(56) References Cited

U.S. PATENT DOCUMENTS 1,596,754 A * 8/1926 Moschelle ............ A61M 27/00
                                                       604/541
1,736,182 A    11/1929 Wilkins
                     (Continued)

FOREIGN PATENT DOCUMENTS

EP           1913926      4/2008
EP         1 790 376      4/2010
WO       2014/145615      9/2014

*Primary Examiner* — Nathan R Price
*Assistant Examiner* — Weng Lee
(74) *Attorney, Agent, or Firm* — Peacock Myers, P.C.; Janeen Vilven

(57) ABSTRACT

A gastric feeding tube and method of use where the tube is of sufficient length for insertion into an esophagus of a subject via the nose or mouth. The gastric feed tube comprises a tube having a distal portion, a middle portion and a proximal portion, an outer surface and an inner surface forming a wall of the tube having a thickness and wherein the wall of the tube defines a lumen of a defined geometry, the lumen having an opening at a distal end of the tube for positioning in a stomach or jejunum of the subject and an opening at the proximal end of the tube for positioning outside of the nose or mouth of the subject wherein the lumen extends longitudinally through the tube connecting the opening at the distal end of the tube and the opening at the proximal end of the tube. The defined geometry of the lumen has a transverse major axis and a transverse minor axis that are perpendicular and wherein a portion of the inner surface of the wall of the tube along the transverse major axis comprises a rib that protrudes into the lumen and thickens the portion of the inner surface of the wall of the tube. The rib prevents the tube from fully collapsing and blocking the lumen when the tube is in use under normal conditions.

19 Claims, 30 Drawing Sheets

(58) Field of Classification Search
CPC ...... A61M 25/0017; A61M 2025/0059; A61M 2210/105; A61M 2025/0025; A61M 27/00; A61J 15/0003; A61J 15/0069; A61J 15/0073; A61J 15/0092; A61J 15/0096
USPC .... 604/27, 36, 514, 516, 257, 523, 524, 270
See application file for complete search history.

(56) References Cited

U.S. PATENT DOCUMENTS

| | | | |
|---|---|---|---|
| 1,928,992 A * | 10/1933 | Masterman | B29D 23/001 138/103 |
| 3,430,631 A | 3/1969 | Abramson | |
| 3,867,946 A * | 2/1975 | Huddy | A61M 16/0666 128/207.18 |
| 3,890,976 A * | 6/1975 | Bazell | A61M 25/0068 128/207.15 |
| 4,257,422 A * | 3/1981 | Duncan | A61M 27/00 138/103 |
| 4,294,535 A | 10/1981 | Ariyama et al. | |
| 4,369,789 A | 1/1983 | LeVeen et al. | |
| 4,388,076 A | 6/1983 | Waters | |
| 4,390,017 A | 6/1983 | Harrison et al. | |
| 4,410,320 A * | 10/1983 | Dykstra | A61J 15/0003 604/270 |
| 4,508,533 A * | 4/1985 | Abramson | A61M 27/00 604/126 |
| 4,610,673 A | 9/1986 | Russo | |
| 4,781,704 A | 11/1988 | Potter | |
| 4,828,550 A | 5/1989 | Kurimoto | |
| 4,863,424 A * | 9/1989 | Blake, III | A61M 25/1027 604/103 |
| 4,874,365 A | 10/1989 | Frederick et al. | |
| 5,324,262 A | 6/1994 | Fischell et al. | |
| 5,370,899 A | 12/1994 | Conway et al. | |
| 5,514,112 A | 5/1996 | Chu et al. | |
| 5,549,579 A | 8/1996 | Batdorf | |
| 5,569,219 A | 10/1996 | Hakki et al. | |
| 5,658,253 A | 8/1997 | Piontek et al. | |
| 5,971,954 A | 10/1999 | Conway et al. | |
| 6,447,472 B1 | 9/2002 | Moss | |
| 6,659,974 B1 | 12/2003 | Moss | |
| 6,984,224 B2 | 1/2006 | McKittrick | |
| 7,125,402 B1 * | 10/2006 | Yarger | A61M 25/0021 604/266 |
| 7,857,750 B2 | 12/2010 | Belafsky | |
| 8,257,306 B2 | 9/2012 | Grathwohl | |
| 2005/0171468 A1 * | 8/2005 | Wood | A61M 1/0058 604/39 |
| 2006/0135915 A1 | 6/2006 | Tucker | |
| 2008/0097350 A1 * | 4/2008 | Bell et al. | 604/266 |
| 2009/0306626 A1 | 12/2009 | Sinha et al. | |

* cited by examiner

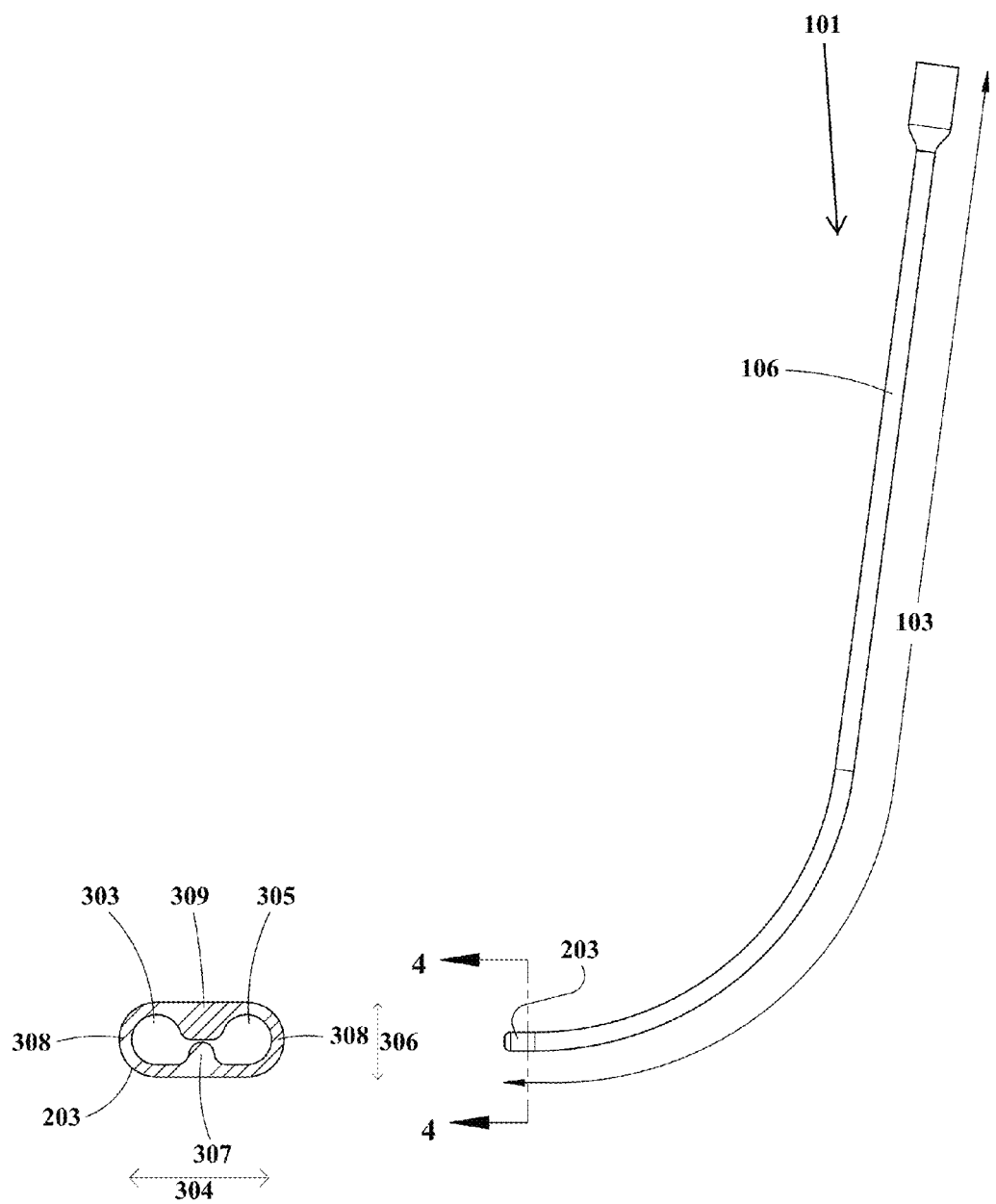

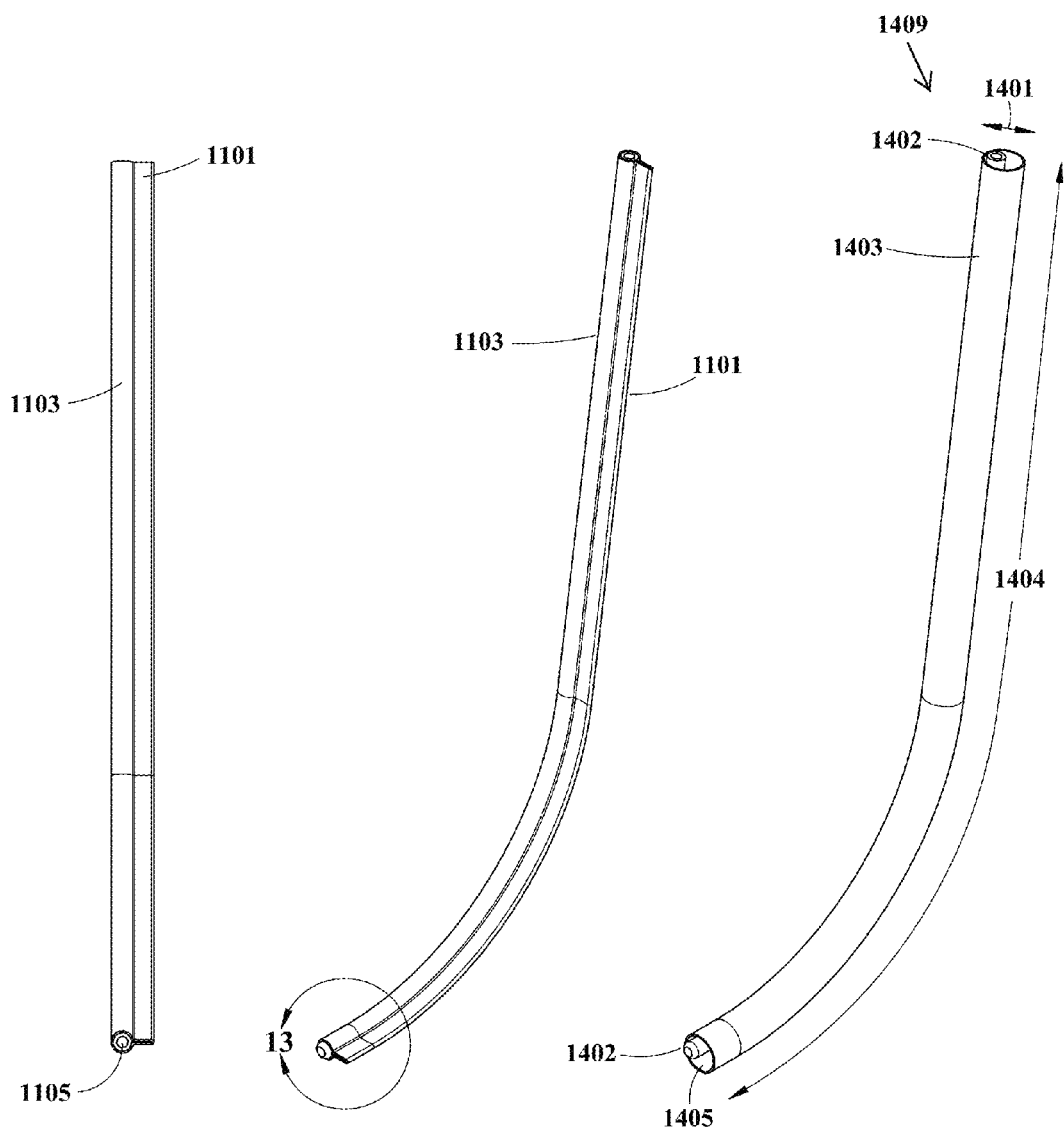
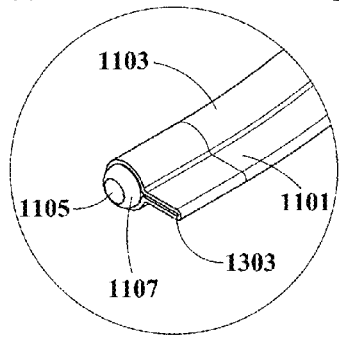
FIG. 11  FIG. 12  FIG. 14
FIG. 13

(OPEN VALVE)

(CLOSED VALVE)

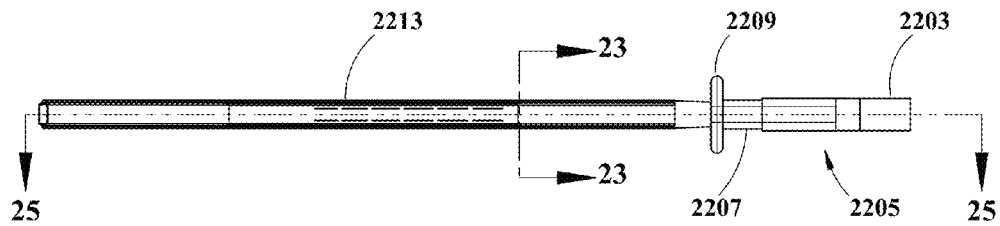
FIG.22
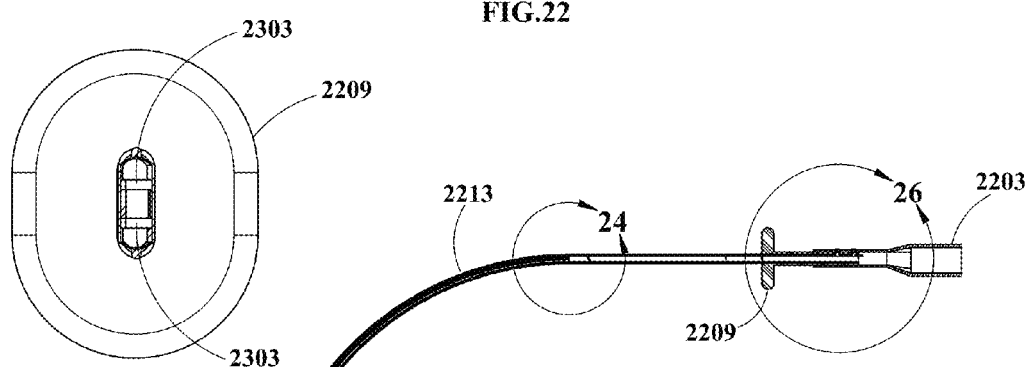
FIG.23
FIG.24
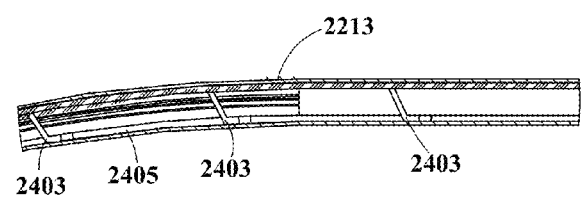
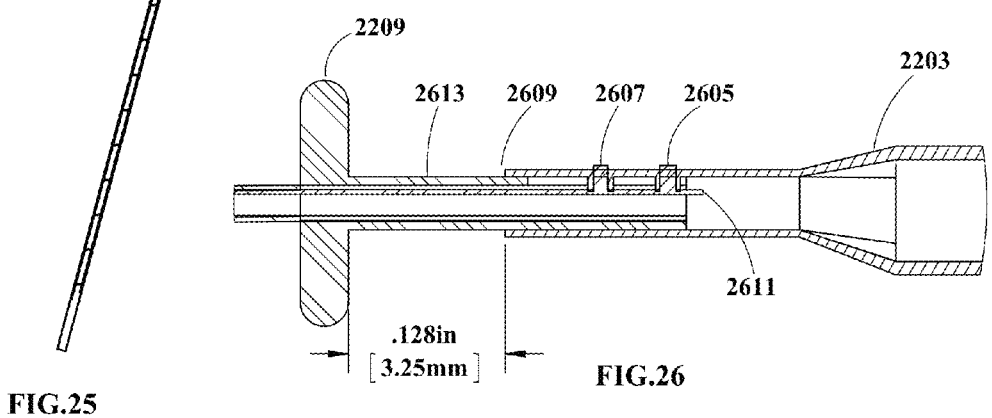
FIG.25
FIG.26

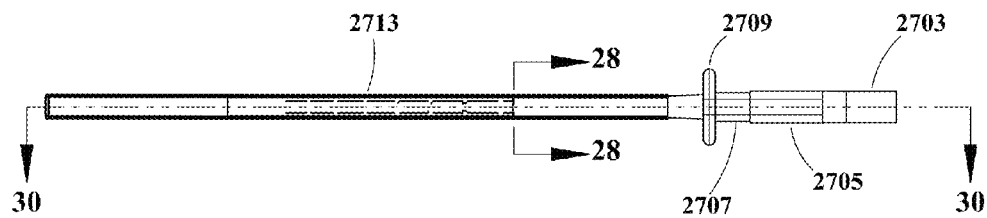
FIG.27
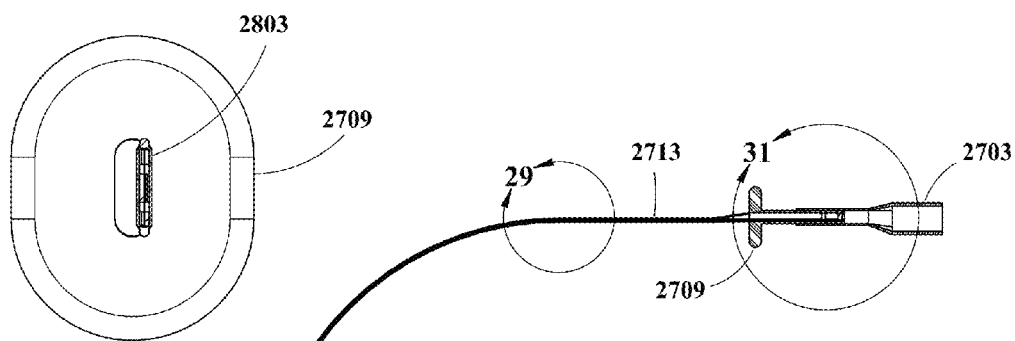
FIG.28
FIG.29
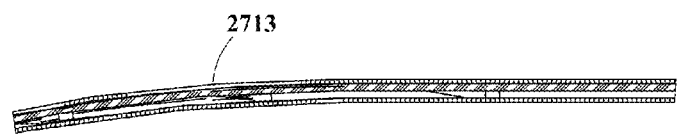
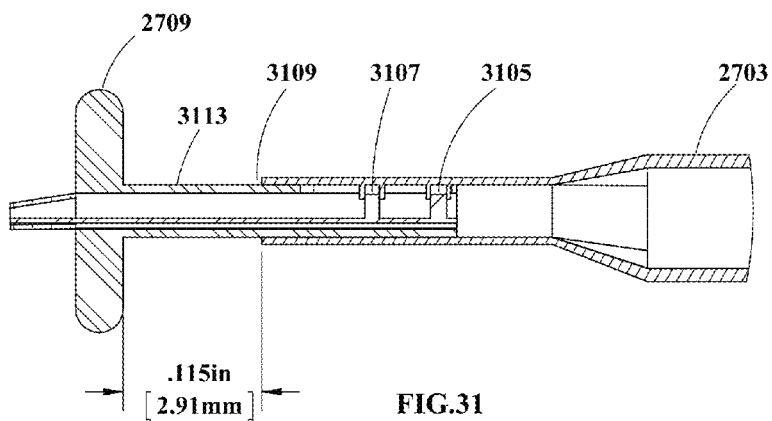
FIG.30
FIG.31

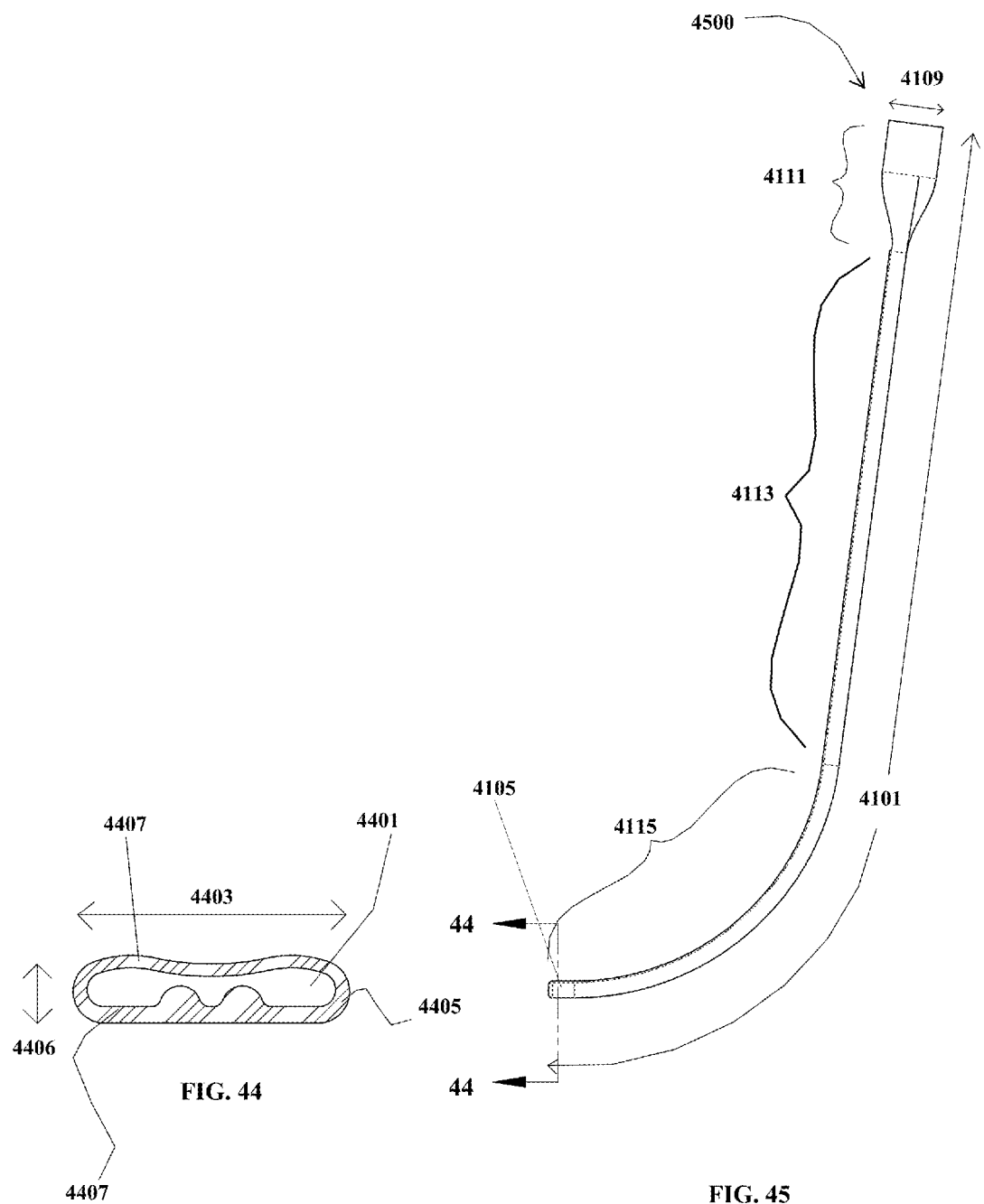

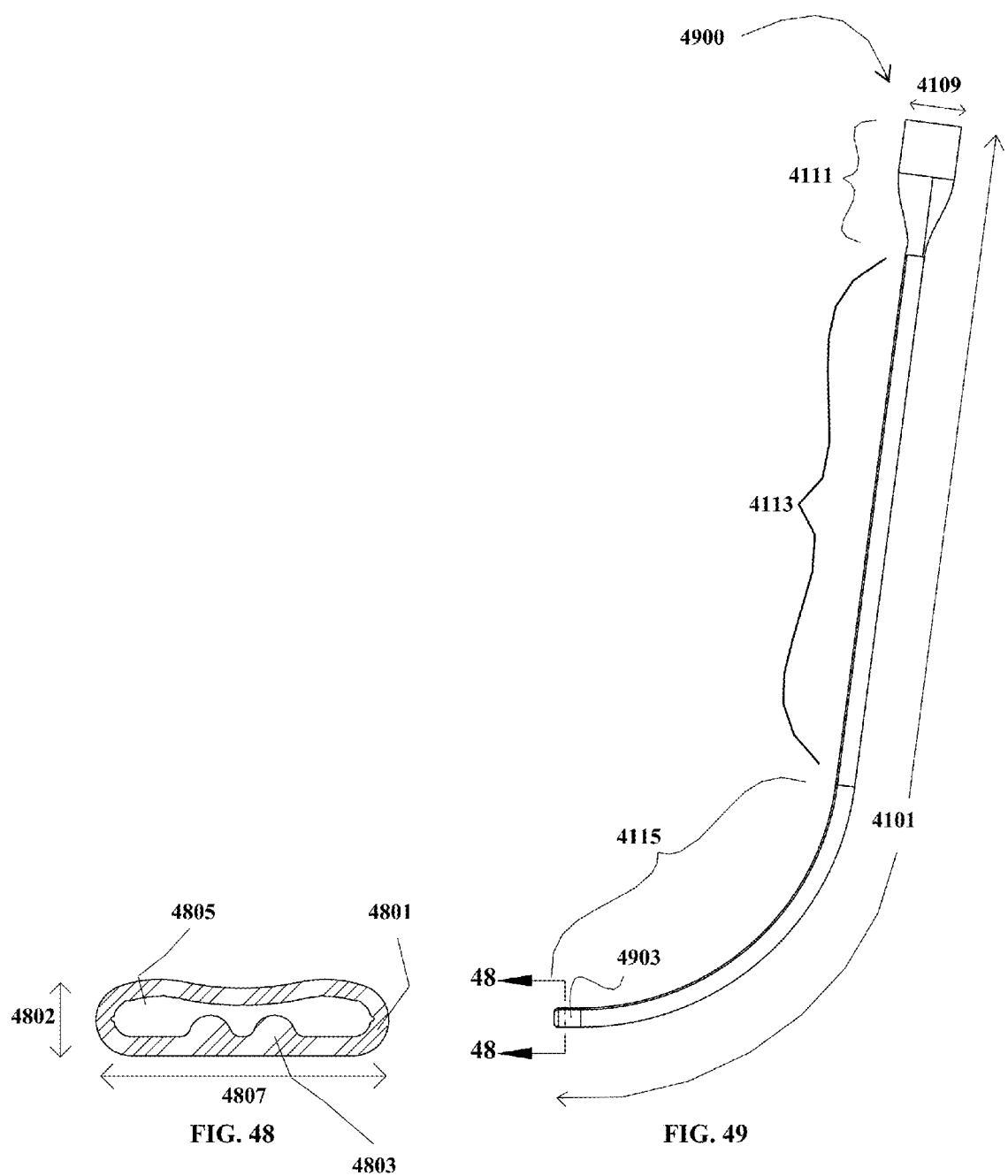

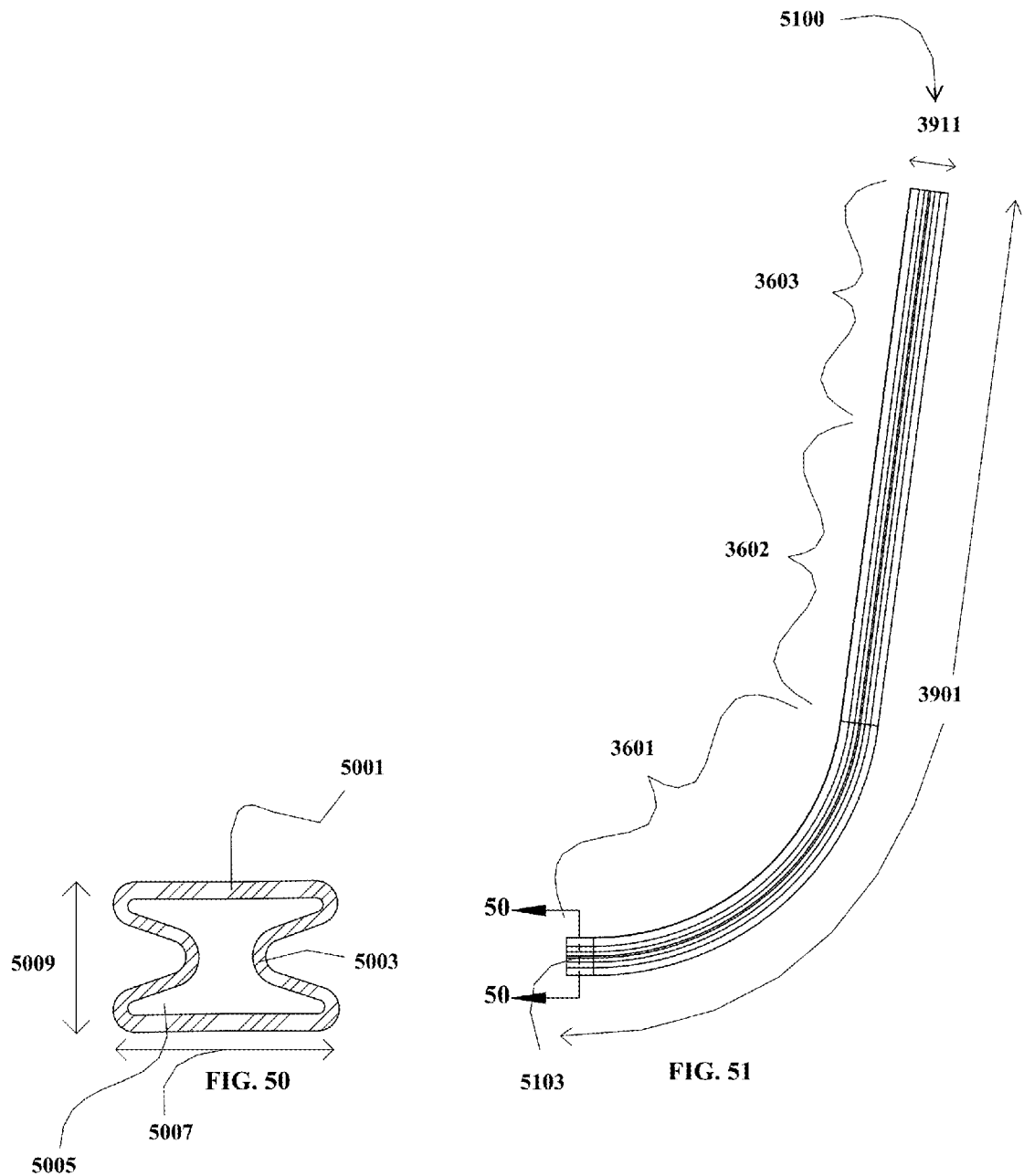

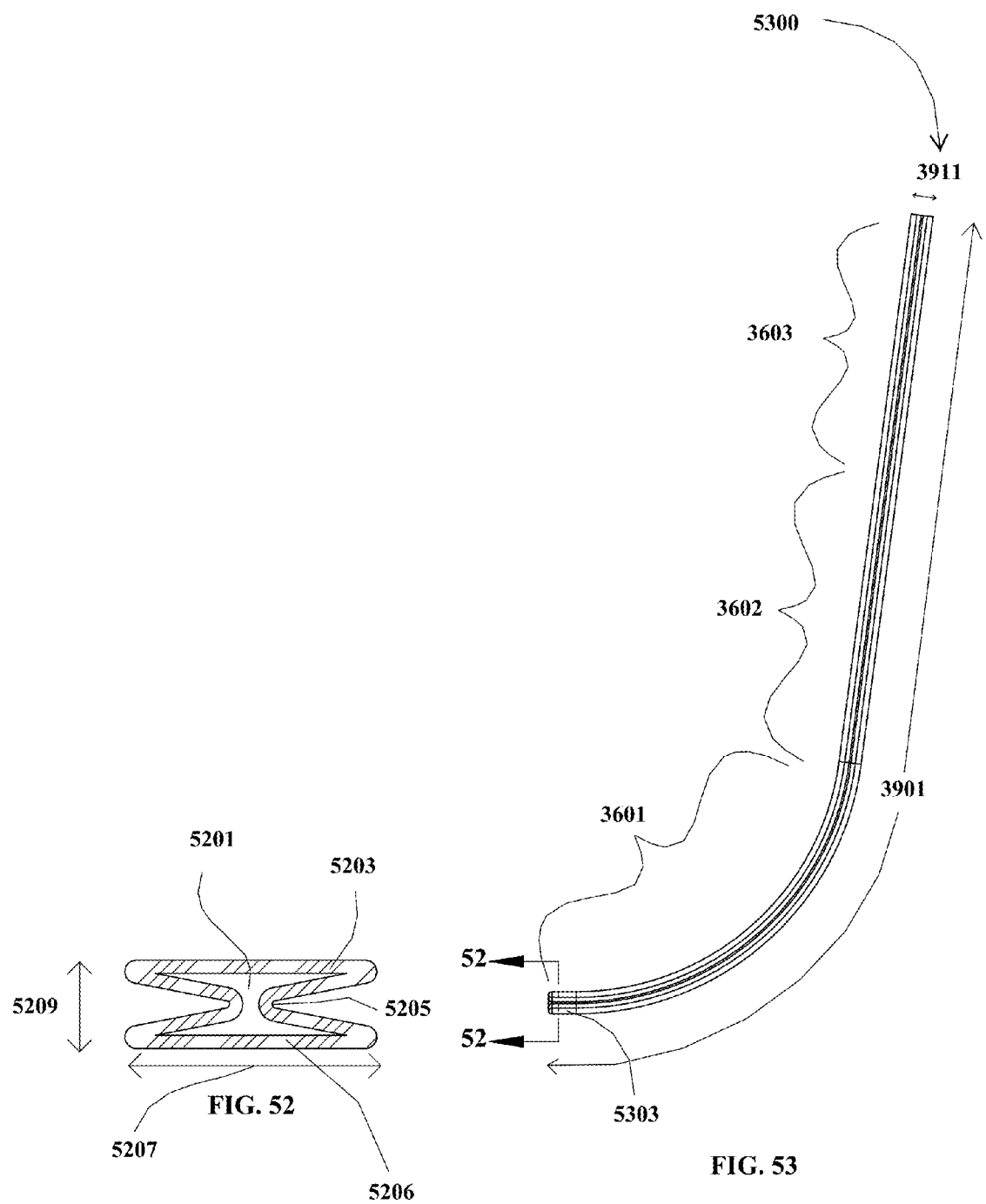

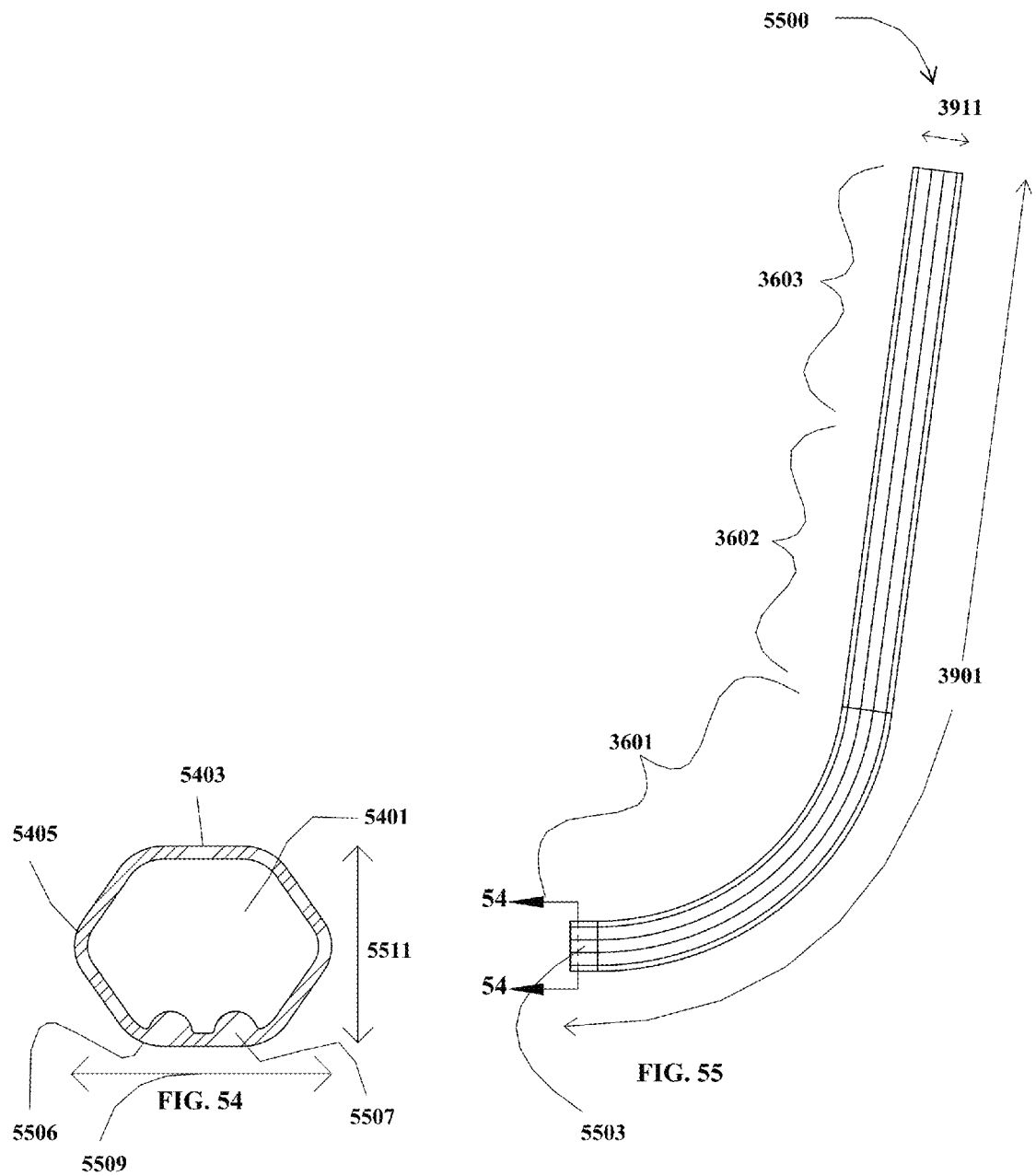

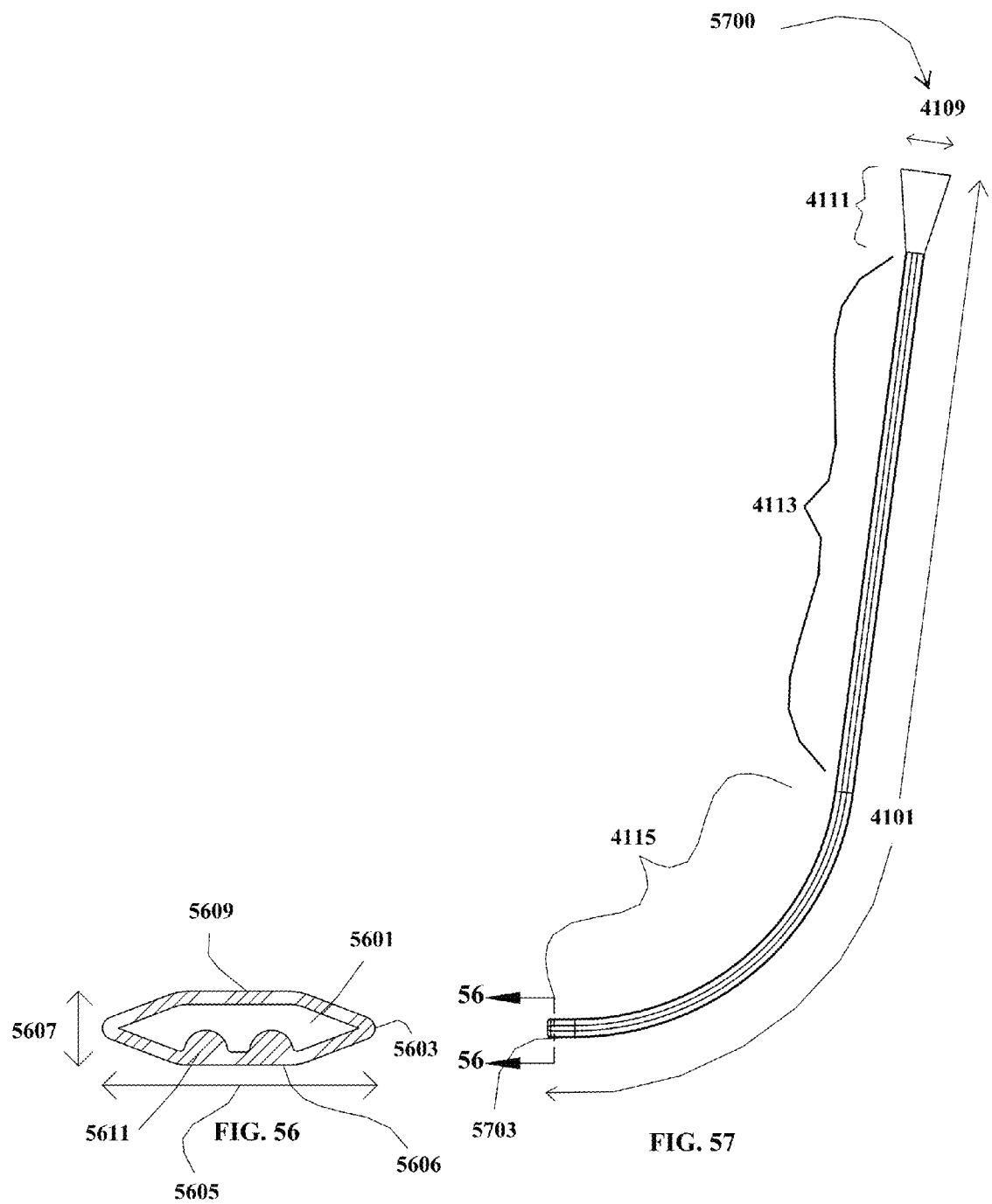

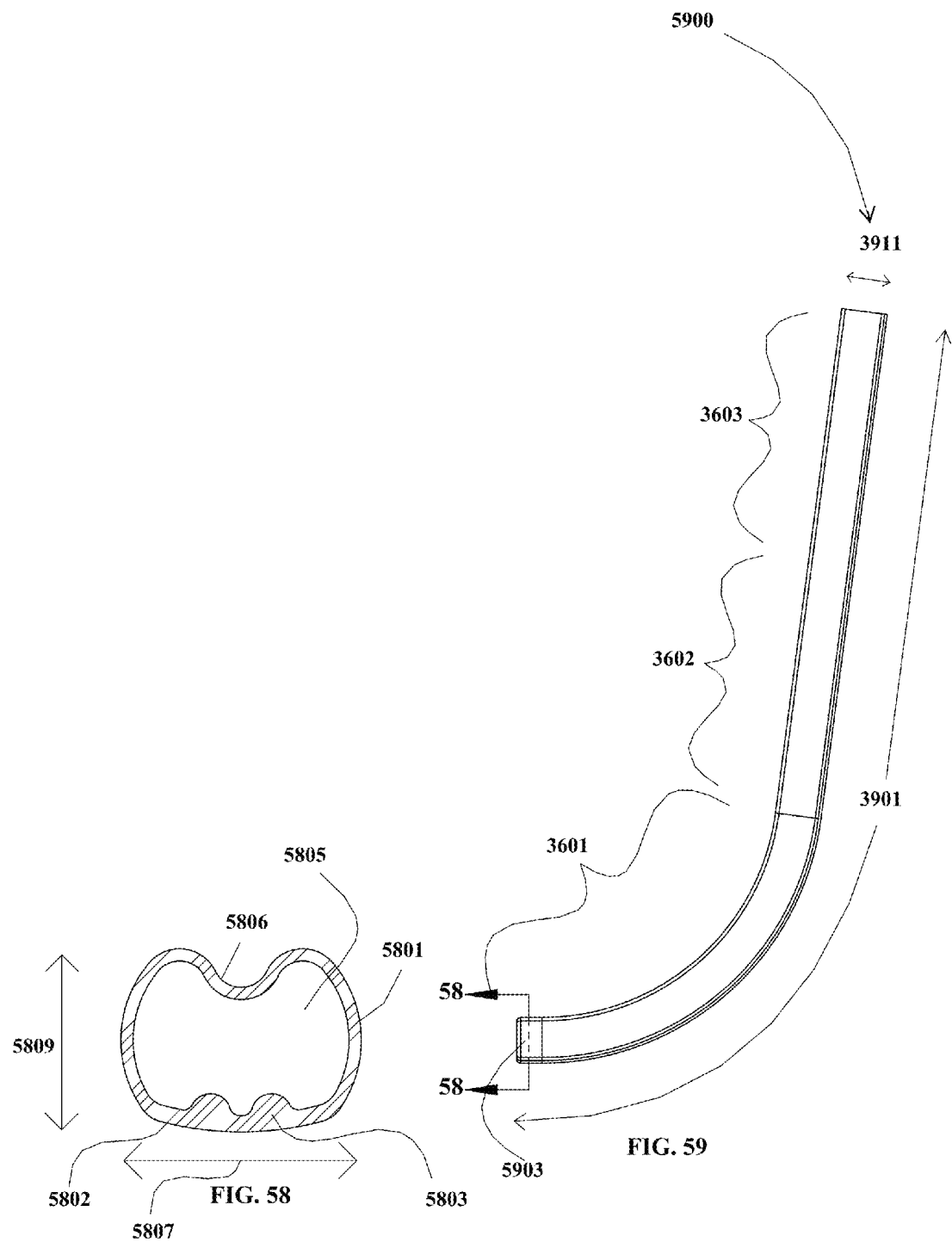

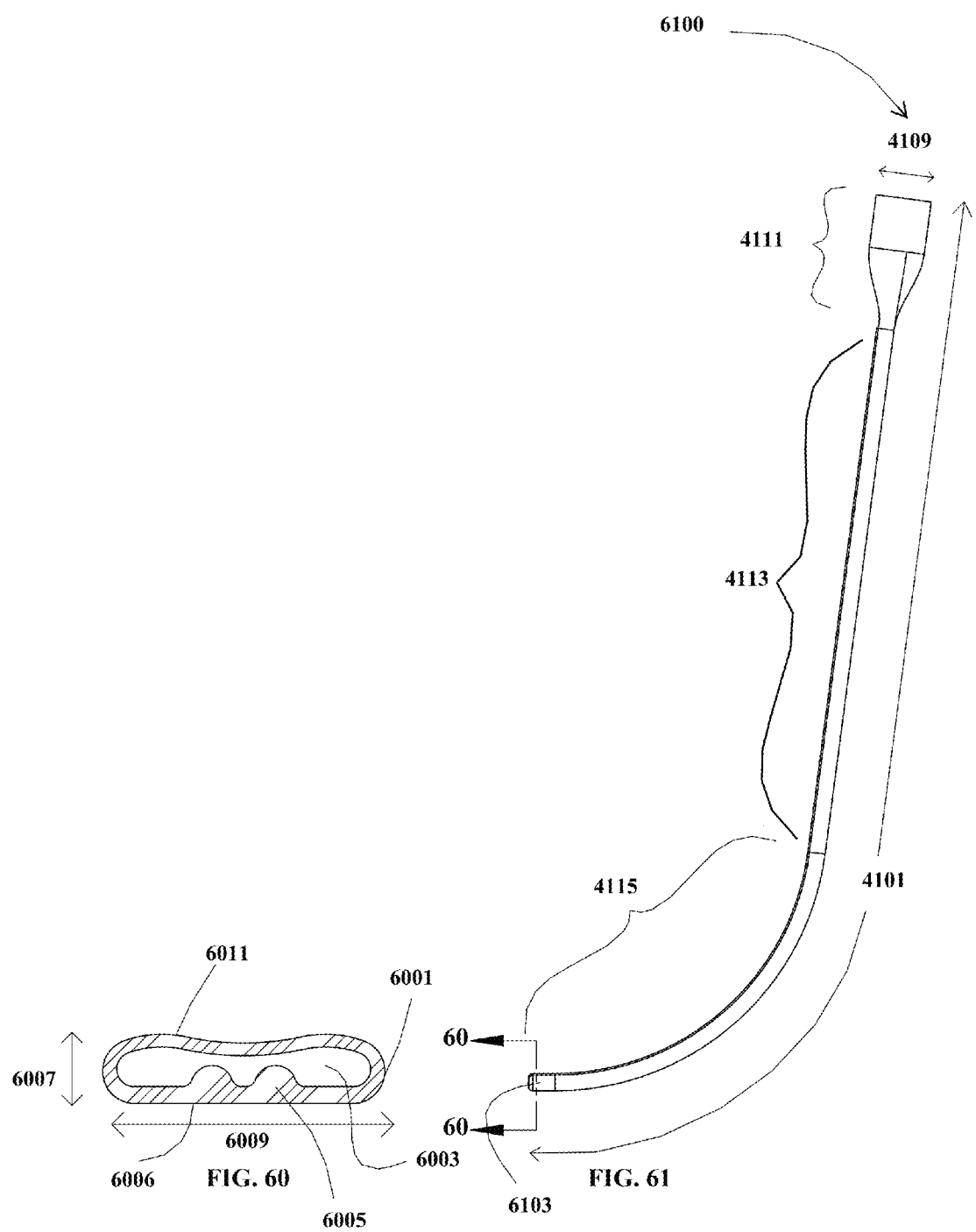

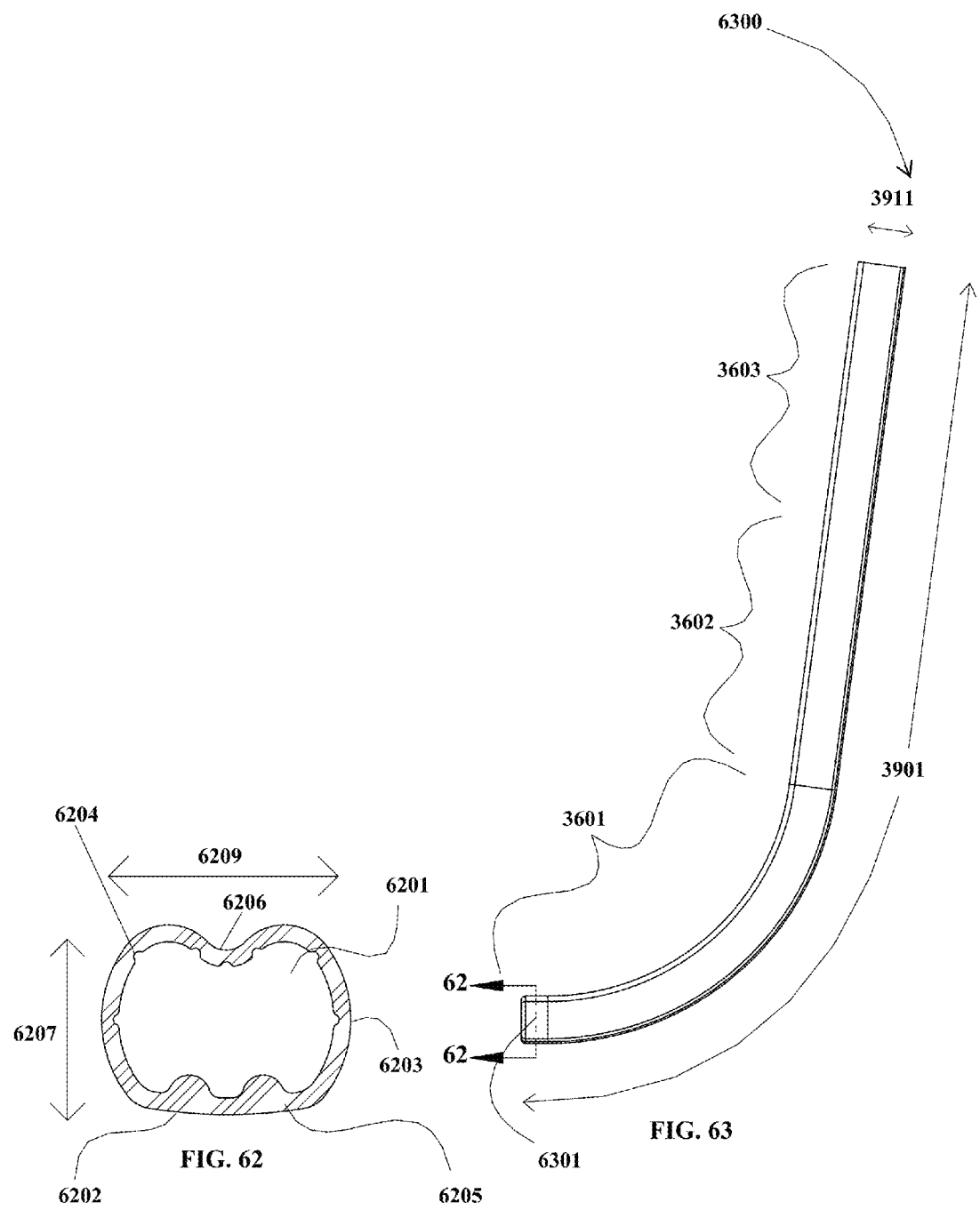

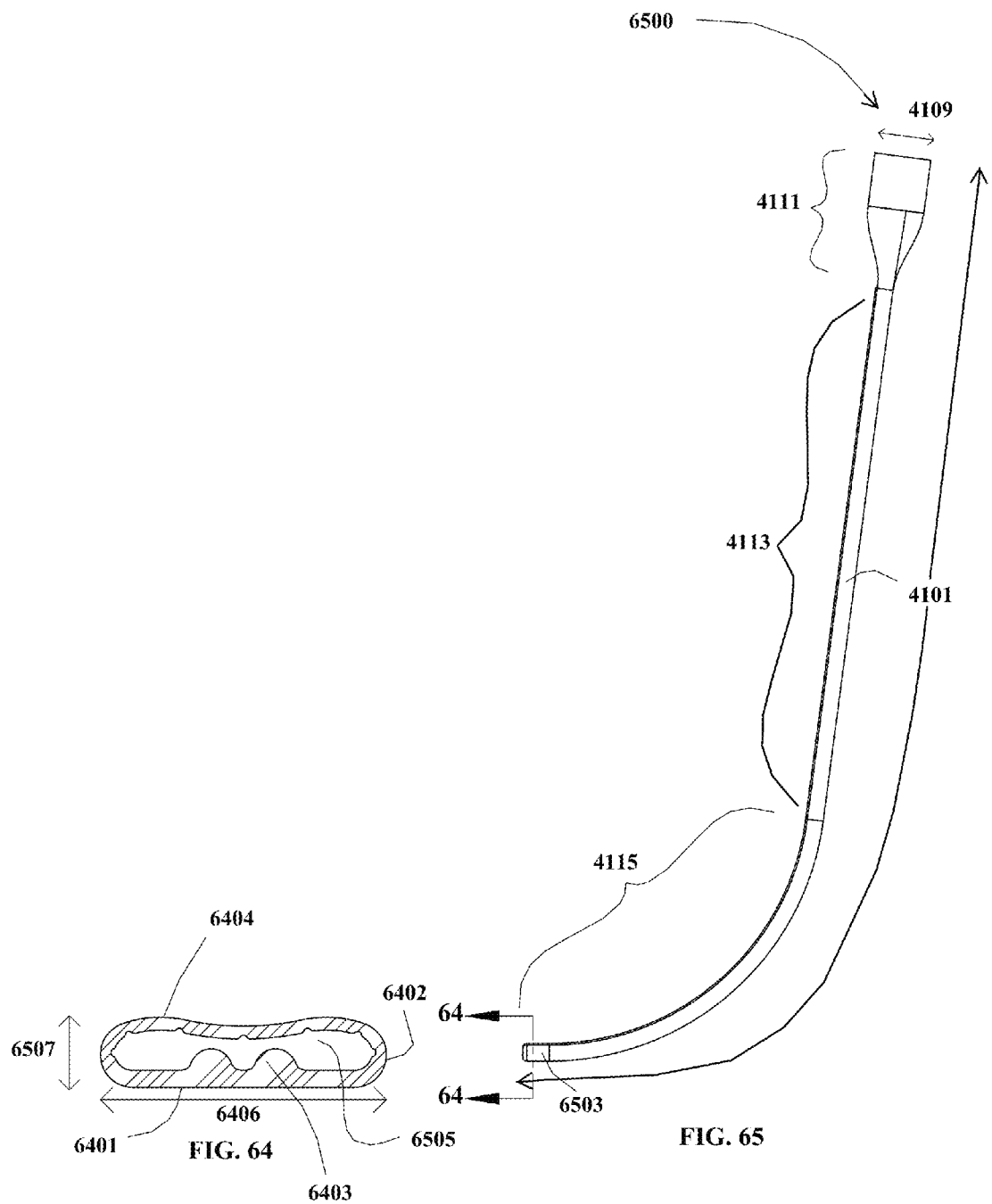

FLUID AND NUTRITION DELIVERY DEVICE AND METHOD OF USE

CROSS-REFERENCE TO RELATED APPLICATIONS

This application claims priority to and the benefit of the filing of U.S. Provisional Patent Application Ser. No. 61/799,496, entitled "FLUID AND NUTRITION DELIVERY DEVICE AND METHOD OF USE", filed on Mar. 15, 2013, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

PARTIES TO A JOINT RESEARCH AGREEMENT

Not Applicable.

SEQUENCE LISTING

Not Applicable.

BACKGROUND OF THE INVENTION

A catheter is a hollow tube for insertion into a cavity, duct, or vessel to allow the passage of fluids or distend a passageway. The catheter includes a tube. During medical treatment it is frequently necessary to rely on a tube that is inserted into a part of the body to inject fluid into the body or drain away fluid or to keep a passage open. For example the tube may be a catheter used to evacuate fluid from a body cavity or organ such as the lungs, pleural cavity, bladder, stomach or chest but not limited thereto. Additionally a catheter can be used to force feed patients who are unable to swallow, or who must be fed continuously with a liquid nourishment substance. Providing the subject with a tube that promotes and allows the subject's natural swallow process to occur is important for comfort.

Some medications, such as those used in the treatment of duodenal ulcers or bleeding stomach ulcers must be introduced directly into the stomach continuously or at frequent intervals. Even if the patient is able to swallow, the schedule of medication necessitates consuming small amounts of medication at frequent intervals, thus preventing sleep and other activities.

In certain feeding situations, the tube is an indwelling oral-nasal gastric tube. These tubes allow food or medication to be administered when a patient is asleep or is unable to swallow. Such tubes are normally introduced through the nose or the mouth and pushed down through the esophagus into the stomach of the patient.

The most common complication which arises in the use of such tubes is necrosis due to tube pressure on the nares. Another common complication is regurgitation of acid peptic stomach contents into the esophagus. This happens because the stomach contents seep alongside the tube into the esophagus. In infants the presence of the tube increases upper airway resistance and predispose the infant to apnea or cessation of breathing. In premature infants the rigidity of the tube may cause indentation of the palate and gums with potential for speech impediment and impaired development of normal future dentition.

The reflux of stomach contents produces a severe esophagitis which can cause stricture or perforation of the esophagus. In order to feed premature infants, post-operative patients with compromised gastro intestinal function, seriously ill patients, or any other patients incapable of normal eating, a gastric feeding tube is usually passed through the nose and esophagus of the patient into the stomach. Since a patient must be fed several times each day, the tube is most generally left in place and the outer proximal end thereof sealed off when not in use. During intubation of a patient, it can be understood that the tubular object is pushed from a position outside the nose or mouth area to locate the distal end of the tube in the patients' stomach.

SUMMARY OF THE INVENTION

One embodiment of the present invention provides a gastric feeding tube of sufficient length for insertion into an esophagus of a subject via the nose or mouth, the gastric feed tube comprises a tube having a distal portion, a middle portion and a proximal portion. The tube has an outer surface and an inner surface defining a wall of the tube of a thickness which thickness may uniform or non-uniform and wherein the wall of the tube defines a lumen of a defined geometry, the lumen having an opening at a distal end of the tube for positioning in a stomach or jejunum of the subject and an opening at the proximal end of the tube for positioning outside of the nose or mouth of the subject. The lumen extends longitudinally through the tube connecting the opening at the distal end of the tube and the opening at the proximal end of the tube. The defined geometry of the lumen has a transverse major axis and a transverse minor axis that are perpendicular and wherein a portion of the inner surface of the wall of the tube along the transverse major axis comprises a rib that protrudes into the lumen and thickens the portion of the inner surface of the wall of the tube as compared to the wall of the tube adjacent to the rib. The wall of the tube along the transverse minor axis is shaped with an outward curve as compared to the wall of the tube along the transverse major axis wherein the outward curve acts as a hinge to permit the tube to partially collapse along the transverse minor axis of the tube when pressure is applied to the outer surface of the tube by the esophagus or upper airway passage to increase an area of the tube along the major transverse axis in contact with the esophagus or upper airway passages. The rib prevents the tube from fully collapsing and blocking the lumen when the tube is in use under normal conditions.

A second embodiment of a gastric feeding tube provides a tube of sufficient length for insertion into an esophagus of a subject via the nose or mouth which comprises a tube having a distal portion, a middle portion and a proximal portion, an outer surface and an inner surface forming a wall of the tube having a thickness and wherein the wall of the tube defines a lumen of a defined geometry, the lumen having an opening at a distal end of the tube for positioning in a stomach or jejunum of the subject and an opening at the proximal end of the tube for positioning outside of the nose or mouth of the subject wherein the lumen extends longitudinally through the tube connecting the opening at the distal end of the tube and the opening at the proximal end of the tube. The defined geometry of the lumen has a transverse major axis and a transverse minor axis that are perpendicular and wherein the portion of the wall of the tube along the transverse major axis comprises a rib that protrudes into the lumen and thickens the portion of the wall of the tube as compared to the wall of the tube adjacent to the rib and wherein the wall of the tube along the transverse minor axis is shaped with an outward curve as compared to the wall of the tube along the transverse major axis. The outward curve acts as a hinge to permit the lumen of the tube to expand along the transverse minor axis of the tube when pressure is applied to the inner surface of the tube by fluid moving in the tube within the esophagus. The rib of the internal wall of the tube along the transverse major axis prevents the tube from fully collapsing and blocking the lumen when the tube is in use as a gastric feeding tube under normal conditions.

A gastric feeding tube as described according to a first or second embodiment of the present invention may be extruded or non-extruded and or formed of a biocompatible material. The embodiment may be flexible. In a further embodiment a weighted tip having lateral ports are formed at the distal end. In an alternative embodiment the proximal end further comprises a connector for coupling to a feeding source. The feeding source may be a pressure driven syringe filled with nutrient or gravity driven receptacle filled with nutrient. The defined geometry of the lumen is consistent along a longitudinal length of the tube. The defined geometry may provide an outer cross section of the tube that is wider along the major axis as compared to the minor axis. The wall of the tube may have increased thickness on one side of the geometry. For example, the thickness of the wall of the tube on one side of the lumen geometry provides stiffness without adding collapse resistance. The rib acts to partially stiffen the tube and the rib may be formed of a higher durometer material as compared to the adjacent wall of the tube.

In one embodiment the tube retains an uncollapsed state in the absence of force. For example, the wall of the tube has sufficient thickness and stiffness to maintain the defined geometry of the lumen in the absence of a deformable force. In another embodiment the tube does not require a stylet or obturator for placement.

In another embodiment the gastric feeding tube of the first or second embodiment acts as an aspiration tube when suction is applied to the proximal end.

One or more embodiments of the present invention provide for a tube outer diameter in the transverse major axis is between 4-14 Fr and the tube outer diameter in the transverse minor axis is between 4-14 Fr. For example the tube outer diameter in the transverse major axis is between 8-14 Fr and the tube outer diameter in the transverse minor axis is between 8-14 Fr. In a preferred embodiment, the tube outer diameter in the transverse major axis is between 6-12 Fr and the tube outer diameter in the transverse minor axis is between 6-12 Fr. In a more preferred embodiment the tube outer diameter in the transverse major axis is between 4-8 Fr and the tube outer diameter in the transverse minor axis is between 4-8 Fr.

In an alternate embodiment the inner surface of the wall of the tube is different as compared to the outer surface of the wall of the tube. Further, the defined geometry of the lumen is not a circle. Additionally, the rib of the inner surface of the wall of the tube along the transverse major axis is a plurality of ribs. For example, the plurality of ribs are located adjacent to each other. Further, the geometry of the outer surface of the wall of the tube along the transverse minor axis of a right side of the tube is the same as a left side of the tube. Alternatively, a geometry of the outer surface of the wall of the tube along the transverse major axis of a bottom side of the tube is the same as a top side of the tube.

In another embodiment, a gastric feeding tube as disclosed herein includes a single lumen or a dual lumen. Further the thickness of the wall surrounding the lumen is diminished at periodic locations of the inner surface of the wall of the tube.

According to another embodiment a method for providing nutrients to a subject with a gastric feeding tube comprises providing a gastric feeding tube according to a first embodiment or a second embodiment or another embodiment disclosed herein having a sufficient length for insertion into an esophagus of a subject via the nose or mouth. The distal end of the gastric feeding tube is positioned in the stomach or jejunum. The liquid nourishment is inserted through the proximal end of the feeding tube located outside of the nose or mouth of the subject. For example, the gastric feeding tube may be inserted into the patient in the absence of a stylet or an obturator according to one embodiment. In an alternate embodiment, the gastric feeding tube may be used to aspirate stomach content from the distal end of the gastric feeding tube without totally collapsing the gastric feeding tube even when the tube is occluded by the stomach content.

It is an object of one embodiment of the present invention to provide a feeding tube to minimize the potential for complications from the feeding tube.

It is another object of an embodiment of the present invention to provide a fluid delivery tube to enhance recovery from inflammatory or obstructive pathological conditions without pressure necrosis of the lumen lining in any physiological/anatomical system such as the GI (esophagus), GU (urinary, urethra), respiratory (nasal).

A feeding tube according to one embodiment of the present invention allows and promotes swallowing skills to naturally develop in premature infants.

It is yet another object of an embodiment of the present invention to provide a drainage tube in post surgical patients.

It is still another object of an embodiment of the present invention to provide a chest tube to drain pleural fluid from the body.

It is a further object of an embodiment of the present invention to provide a paracentesis tube for use in medical procedures.

It is a further object of the present invention to provide a catheter that is designed to partially collapse in a preferred orientation which collapse is reversible.

It is a further aspect of the present invention to provide a feeding tube to allow for swallowing behavior learning by presenting little resistance to the anatomy during swallowing.

It is an additional object of an embodiment of the present invention to provide a medical catheter for evacuation of accumulated body fluids.

It is an aspect of an embodiment of the present invention to provide a feeding tube that does not prevent a subject from swallowing naturally when the tube is in place. Swallowing is the process in the human or animal body that makes something pass from the mouth, to the pharynx, and into the esophagus, while shutting the epiglottis.

One aspect of an embodiment of the present invention provides for a flexible feeding tube which does not require an obturator for placement. For example the feeding tube includes a guide support element that is within the side of the tube and non-separatable from the tube.

It is an additional aspect of an embodiment of the present invention to provide for a flexible tube which does not include an inflatable outer diameter to open a lumen of the tube. It is a further aspect of an embodiment of the present invention to provide a feeding tube that does not have an inflation space between an inner wall and an outer wall. It is an additional aspect of the present invention to provide a feeding tube without a balloon means for collapsing or partially stiffening the tube and wherein the feeding tube remains in a state of open but is partially collapsible under normal use. It is another aspect of the present invention to provide a tube that is flexible and can easily be shaped into a curved geometry or straight geometry along its length. The flexibility of the tube allows for it to be easily guided from the proximal end through a tortuous path.

It is yet another aspect of the present invention to provide a tube with a weighted tip to facilitate placement of the tube in the correct location and or to maintain its location.

It is another object of the present invention to provide an irrigation tube for use in irrigation systems, moisture control environments such as flower beds and golf greens.

Additional objects and advantages of the present invention will be apparent in the following detailed description read in conjunction with the accompanying drawing figures.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 3 illustrates a fluid delivery tube according to one embodiment of the present invention.

FIG. 4 illustrates a distal end portion of a fluid delivery tube of FIG. 2 according to one embodiment of the present invention.

FIG. 11 illustrates a fluid delivery tube according to one embodiment of the present invention.

FIG. 12 illustrates a fluid delivery tube according to one embodiment of the present invention.

FIG. 13 illustrates a distal end of a fluid delivery tube of FIG. 12 according to one embodiment of the present invention.

FIG. 14 illustrates a fluid delivery tube according to one embodiment of the present invention.

FIG. 22 illustrates a top view of a fluid delivery tube of FIG. 21 according to one embodiment of the present invention.

FIG. 23 illustrates a sectional of a fluid delivery tube of FIG. 22 according to one embodiment of the present invention.

FIG. 24 illustrates a fluid delivery tube cross section of FIG. 25 according to one embodiment of the present invention.

FIG. 25 illustrates a fluid delivery tube sectional view of FIG. 22 according to one embodiment of the present invention.

FIG. 26 illustrates a detailed view of a fluid delivery tube of FIG. 25 according to one embodiment of the present invention.

FIG. 27 illustrates a fluid delivery tube according to one embodiment of the present invention.

FIG. 28 illustrates a sectional view of a fluid delivery tube of FIG. 27 according to one embodiment of the present invention.

FIG. 29 illustrates an expanded view of a section of the fluid delivery tube of FIG. 30 according to one embodiment of the present invention.

FIG. 30 illustrates a cross section of fluid delivery tube of FIG. 27 according to one embodiment of the present invention.

FIG. 31 illustrates an expanded view of a section of the fluid delivery tube of FIG. 30 according to one embodiment of the present invention.

FIG. 44 illustrates an enlarged view of area 44 of the distal end of the tube of FIG. 45.

FIG. 45 illustrates a fluid delivery tube according to one embodiment of the present invention.

FIG. 48 illustrates an enlarged view of area 50 of the distal end of the tube of FIG. 49.

FIG. 49 illustrates a fluid delivery tube according to one embodiment of the present invention.

FIG. 50 illustrates a view of the distal end of the tube of FIG. 51.

FIG. 51 illustrates a side view of a fluid delivery tube according to one embodiment of the present invention.

FIG. 52 illustrates an enlarged view of area 52 of the distal end of the tube of FIG. 53.

FIG. 53 illustrates a side view of a fluid delivery tube according to one embodiment of the present invention.

FIG. 54 illustrates an enlarged view of area 54 of the distal end of the tube of FIG. 55.

FIG. 55 illustrates a side view of a fluid delivery tube according to one embodiment of the present invention.

FIG. 56 illustrates an enlarged view of area 56 of the distal end of the tube of FIG. 57.

FIG. 57 illustrates a side view of a fluid delivery tube according to one embodiment of the present invention.

FIG. 58 illustrates an enlarged view of area 58 of the distal end of the tube of FIG. 59.

FIG. 59 illustrates a side view of a fluid delivery tube according to one embodiment of the present invention.

FIG. 60 illustrates an enlarged view of area 60 of the distal end of the tube of FIG. 61.

FIG. 61 illustrates a side view of a fluid delivery tube according to one embodiment of the present invention.

FIG. 62 illustrates an enlarged view of area 62 of the distal end of the tube of FIG. 63.

FIG. 63 illustrates a side view of a fluid delivery tube according to one embodiment of the present invention.

FIG. 64 illustrates an enlarged view of area 64 of the distal end of the tube of FIG. 65.

FIG. 65 illustrates a side view of a fluid delivery tube according to one embodiment of the present invention.

DETAILED DESCRIPTION OF THE INVENTION

Figure 1:
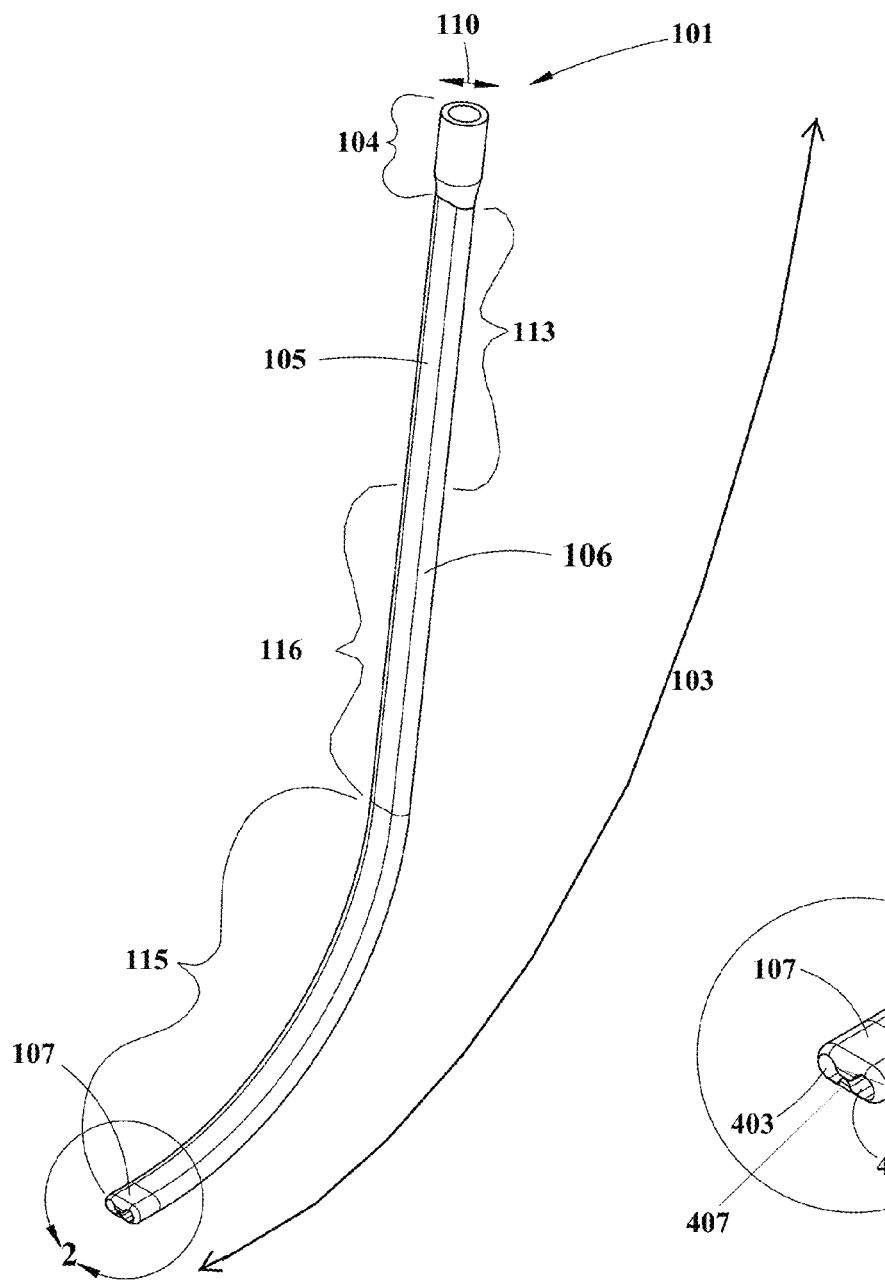
FIG. 1 illustrates a fluid delivery tube according to one embodiment of the present invention.

Referring now to one or more embodiments of the present invention, catheters may be constructed of flexible unitary elongated tube with defined cross section, for example oval, hexagonal or irregular geometries. An embodiment may have a single lumen formed of tube walls or sides with at least one internal rib that keeps the tube from flattening completely on aspiration. A rib is a thickening in the wall of the tube as compared to the adjacent wall of the tube. The rib extends into the lumen. The location of the one or more ribs, for example two ribs that are located adjacent, creates a spine of the tube which provides more rigidity to the tube than in the absence of the ribs. The rib(s) function to prevent the total collapse of the tube as the rib(s) creates a point of contact to keep the opposing inner-surface of the tube wall from laying flat against the full length of the side of the tube having the ribs. The ribs allow the formation of pockets or pathways along the longitudinal length of the lumen even when the tube is in the relaxed conformation or during total or partial collapse of the tube from an expanded conformation. For example a pinched or kinked tube of about 9FR OD in the major axis and 8FR OD in the minor axis may keep up to 7% open area in its lumen and tests have shown that even with only 7% open lumen available, aspiration of fluid through the lumen of the tube is still possible. The outer cross section of tube is wider in one direction (major axis) than another (minor axis) to keep a lower profile of the tube when in use and to minimize local stress concentrations against internal anatomy. For example, the stress (force/area) on the tissue exerted by the side of the tube along the major axis as it contacts the anatomy is less if the tube contacts a greater area of the anatomy as compared to the same force applied to a smaller area of the anatomy by a smaller area of a tube. When the force is the same but distributed over a larger area of the anatomy there is less local stress. In one embodiment when the tube is used as a nasal-gastric feeding tube, the feeding tube expands under pressure of feeding (through pressure created, for example, by head height, pump, or syringe injection). In one embodiment, during aspiration, the rigid elements (for example the rib(s)) and or protrusions keep the feeding tube open. During aspiration the cross-section of the feeding tube may be reduced due to the collapse of the sides of the tube along the minor axis as fluid is removed from the length of the tube and if negative pressure is created. In contrast the cross-section of the feeding tube during feeding is greater as the volume of material passing in the tube for feeding acts to keep the tube expanded. In one embodiment, the tube contains a thicker portion or rib in the side of the tube along the major axis. When the tube is positioned in the esophagus the side of the tube with the tub can be oriented anterior, posterior or another orientation. In an alternative embodiment, the thicker wall sections of the tube are located on each end of the side along the major axis with a thinner section located between the two ribs or in the middle of the wall on the major axis. Alternative cross-section geometries are possible such as multiple ribs along the longitudinal axis of a tube with the cross section geometry of the lumen including a curve, for example oblong, oval, round, octagonal or hexagonal internal geometry for example but not limited thereto. In a preferred embodiment, ribs are adopted for extruded tubes and non extruded tubes. A connector may be formed at the proximal end of the tube from extrusion (single component part) over-molded or adhesive bonded luer connection for example. Materials from which the tube may be fabricated include: Polyurethane, and Silicone but not limited thereto.

In one embodiment the tube is extruded of a biocompatible polymer acceptable for insertion into the human body.

Referring now to FIG. 1, a tube for medical use is illustrated according to one embodiment of the present invention. In a preferred method of use the tube is used for gastric feeding. An opening at the proximal end 113 of tube 101 has connector 104. Connector 104 can be coupled to a syringe or other device to deliver fluid to the tube or for applying a suction to the tube to remove fluid from the body (ex. Stomach contents). In an alternative embodiment no connector is required. Tube side 105 is flatter and wider on a side as compared to tube side 106 which is more rounded and less wide in comparison to tube side 105. The backside of the tube (not shown) is the same as tube side 105. The far side of the tube is the same as tube side 106. The proximal end of the tube 113 is connected to the distal end of the tube 115 by the central portion of the tube 116. The curve is flexible and may be curved or bent anywhere along its length. The tube has a longitudinal axis 103 and a lateral axis 110. The longitudinal axis is intended to extend through the passageways of the body for example. The longitudinal axis is greater than the transverse axis of the tube. The distal tip of the tube 107 is positioned in the stomach of a patient when the tube is used as a feeding or gavage tube. Area 2 is illustrated in FIG. 2.

A size for a standard newborn feeding tube is about 5-10 french OD. A newborn esophagus is about 15 french. Because of the oval shape of the one or more embodiments of a device the lumen can be wider than the standard feeding tube and still have less pressure on the tissue. Feeding from top down will expand walls outward and the sides of the major axis move away from each other to maintain one lobe. When aspirating, the ridges will move toward each other and two lobes will form as the rounded sides collapse partially. The walls of the tube will not fully collapse under low pressure aspiration of fluid. The architecture of the tube and the material from which it is manufactured allows the tube to coil like a hose as the tube may be flexible.

Figure 2:
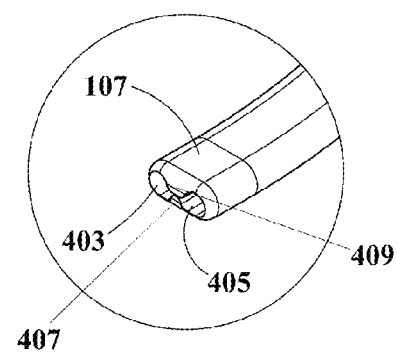
FIG. 2 illustrates an enlarged view of the distal end of a fluid delivery tube of FIG. 1 according to one embodiment of the present invention.

Referring now to FIG. 2, the distal end 107 of tube 101 is illustrated. Rib 407 and protrusion 409 (sometimes referred to as ridges) extend toward each other. A first lobe 403 and a second lobe 405 of the tube is shown with rib 407 and 409 located between first lobe 403 and second lobe 405.

Referring now to FIG. 3, a side view of the tube of FIG. 1, as described in FIG. 1, is illustrated according to one embodiment of the present invention. The tube 101 is turned so that the side 106 along the minor axis is shown. The distal tip of the tube 203 of area 4 is shown expanded in FIG. 4.

Referring now to FIG. 4, an end on view of the distal opening 203 of the tube 101 is illustrated according to one embodiment of the present invention. The opening consists of a first lobe 303 and a second lobe 305 formed between side wall 308 and wall 203 having a rib 307 and wall 309 having a protrusion that acts to thicken wall 309 and 203. Wall 308 is thinner than wall 203 and wall 309. The first lobe 303 and the second lobe 305 are in communication via a passage that exists between the two lobes when the tube is in a relaxed state and not stretched. The minor axis 304 and the major axis 306 of the distal opening is illustrated.

Figures 5, 6:
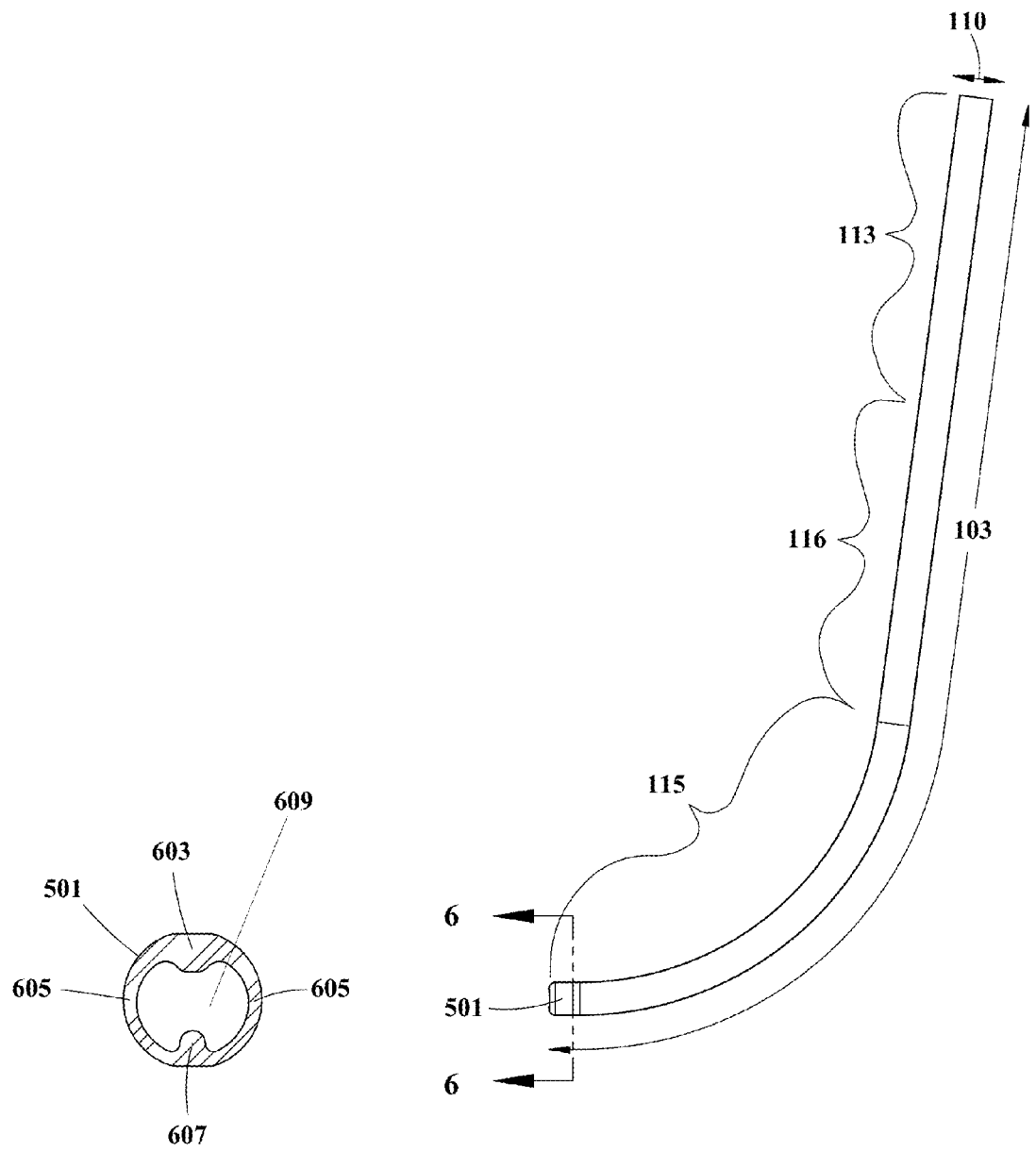
FIG. 5 illustrates a fluid delivery tube according to one embodiment of the present invention.
FIG. 6 illustrates a distal end portion of a fluid delivery tube of FIG. 5 according to one embodiment of the present invention.

Referring now to FIG. 5 an embodiment of a feeding tube is provided as described in FIG. 1 wherein distal end 501 of area 6 is illustrated in FIG. 6.

Referring now to FIG. 6, the distal end of the tube 501 is illustrated in an expanded view wherein the lumen 609 of the distal end of the tube in the minor axis is larger due to fluid for feeding entering the tube and expanding the lumen formed by walls 603, 607 and 605 from the relaxed state shown in FIG. 4 for walls 307 and 309 and 308. As wall 603 and wall 607 are expanded outward, first lobe 303 and the second lobe 305 of FIG. 4 are replaced by lobe 609 which is larger than either the first lobe 303 or the second lobe 305 individually.

Figures 7, 8:
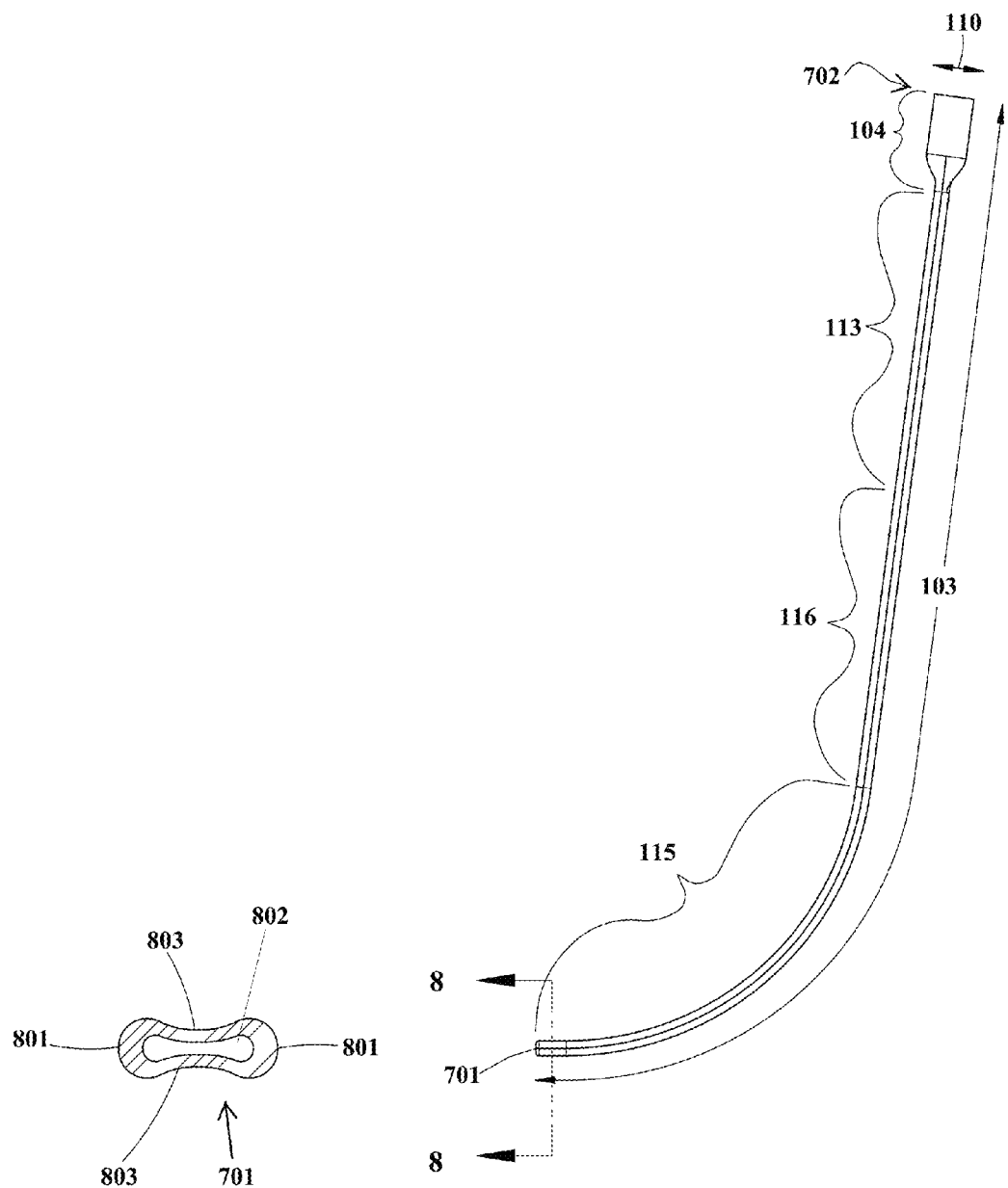
FIG. 7 illustrates a fluid delivery tube according to one embodiment of the present invention.
FIG. 8 illustrates a distal end portion of a fluid delivery tube of FIG. 8 according to one embodiment of the present invention.

Referring now to FIG. 7, an embodiment of the present invention of a feeding tube 702 is provided as described in FIG. 1 wherein area 8 of distal end 701 is illustrated in FIG. 8.

Referring now to FIG. 8, a cross section view of distal end 701 is illustrated. Wall 801 is thicker as compared to wall 803 in the relaxed state of the lumen 802 of the tube wherein the opening of the lumen 802 of the tube is elongated.

Figures 9, 10:
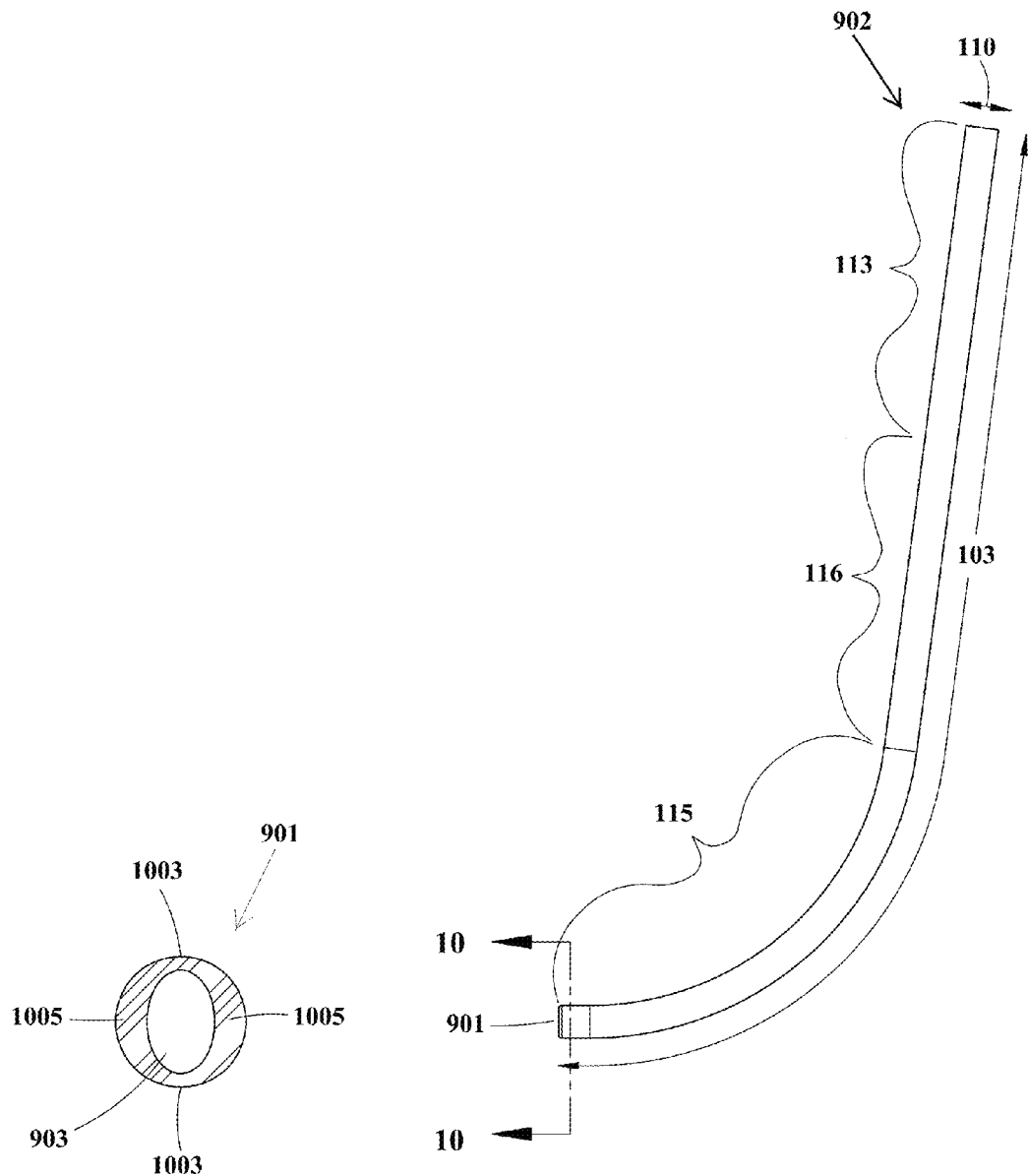
FIG. 9 illustrates a fluid delivery tube according to one embodiment of the present invention.
FIG. 10 illustrates a distal end portion of a fluid delivery tube of FIG. 9 according to one embodiment of the present invention.

Referring now to FIG. 9, an embodiment of the present invention of feeding tube 902 is provided as described in FIG. 1 with area 10 at distal end 901 of tube 902 illustrated in FIG. 10.

Referring now to FIG. 10, the lumen 903 of the distal end 901 of tube 902 is shown in the expanded stated. The expanded state arises when fluid is being delivered to the stomach for feeding. Wall 1005 is thicker than wall 1003 in the expanded state with the lumen 903 being larger and having a circular shape as compared to the lumen in FIG. 7 representing the relaxed stated of the lumen.

Referring now to FIG. 11, a feeding tube with an aspiration tube is illustrated. A flexible film feeding tube 1101 adjoins a rigid aspiration tube 1103 according to one embodiment of the present invention. According to one embodiment the flexible film tube is partially fixed to the rigid tube. Flexible film portion 1101 of the tube lays flat when not in use. Aspiration tube 1103 is smaller than standard feeding tubes. Flexible portion 1103 inflates under hydraulic pressure. Feeding may be delivered through either, the aspiration tube 1103, the flexible film feeding tube 1101 or both. According to one embodiment, aspiration is performed through the aspiration tube 1103 only. According to one embodiment, an introducer is used to introduce the feeding tube to its location for example into the patient. An introducer may have a solid core that fits within rigid or flex tube. An outer sheath that covers both tubes is removed after placement. The distal end of the feeding tube 1105 is rounded. The flexible film feed tube is collapsible around the rigid aspiration tube. The flexible film feeding tube may expand around the aspiration tube to maximize the cross sectional area for fluid delivery.

Referring now to FIG. 12, the feeding tube of FIG. 11 is illustrated in a perspective view. The flexible film feeding tube 1101 is flatter than the aspiration tube 1103. Area 13 is illustrated in FIG. 13.

Referring now to FIG. 13, an enlarged view of the distal end 1105 of the feeding tube of FIG. 12 is illustrated. Tip portion 1107 is shown rounded or tapered. Adjacent to feeding tube 1103 is flexible film feeding tube 1101 has end 1303 which may expand when fluid for feeding is introduced into the lumen of feeding tube 1101. In one embodiment the aspiration tube is about 3-10 French OD.

Referring now to FIG. 14, a feeding tube is illustrated according to one embodiment. Tube assembly 1409 has a lateral axis 1401 and longitudinal axis 1404. Internal tube 1402 is located within external tube 1403 having distal opening 1405.

Figure 15:
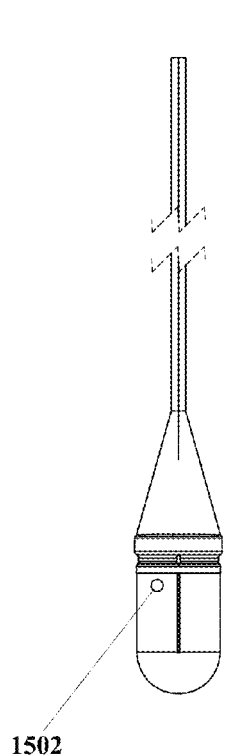
FIG. 15 illustrates a fluid delivery tube according to one embodiment of the present invention.

Referring now to FIG. 15, an illustration of a venturi tube is illustrated according to one embodiment of the present invention. A port 1502 for allowing feeding fluid to enter the stomach is provided.

Figure 16:
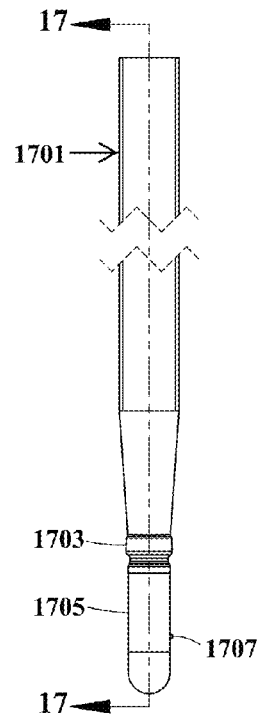
FIG. 16 illustrates a fluid delivery tube according to one embodiment of the present invention.

Referring now to FIG. 16, an illustration of a venturi tube 1701 is illustrated according to one embodiment of the present invention. Connector 1703 connects the tubes to the distal tip 1705 having port 1707. Area 17 is illustrated in FIG. 17.

Figure 17:
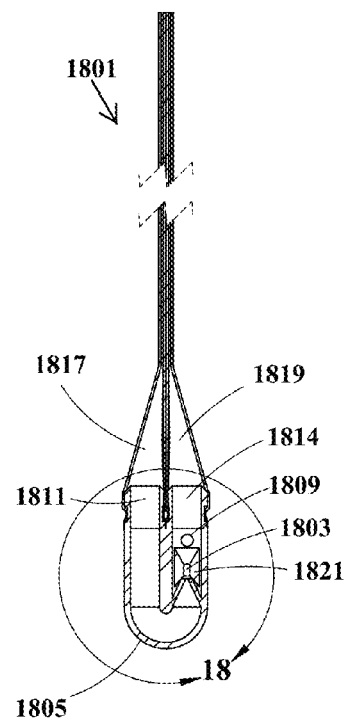
FIG. 17 illustrates a fluid delivery tube according to one embodiment of the present invention.

Referring now to FIG. 17 a feeding tube 1801 having a venturi chamber 1805 at the distal end is illustrated. A venturi feeding tube according to one embodiment comprises two flat films at the proximal end each having a lumen 1817 and 1819 through which fluid passes. The lumens 1817 and 1819 each widens upon connecting to a separate chamber a first chamber 1811 and a second chamber 1814. The distal end includes a rigid plastic tip housing venturi chambers. It is a venturi feature to locally increase flow and create a region of low pressure. A check valve 1707 (FIG. 16) permits flow inwards to the device but not out (to prevent inflation of stomach). A movable element 1821 that closes a feeding port (1809) when venturi is active but opens when feeding fluids are presented in the second lumen and into the second chamber 1819 may be included. Films of tube 1701 lay flat in esophagus and throat when not in use. Fluids are injected into the first lumen to create venturi effect at tip, pulling in stomach contents. Feeding fluids exit through port 1809 of second chamber 1814. Venturi pressure/flow keep feeding port shut while check valve protects against blocked exhaust lumen ($2^{nd}$ lumen). To feed, fluids are introduced through the $2^{nd}$ lumen into the second chamber causing an internal member 1821 in the distal tip to shift downwards and open a feeding port 1809. An expanded view of the venturi feeding tube of area 18 is illustrated in FIG. 18.

Figure 18:
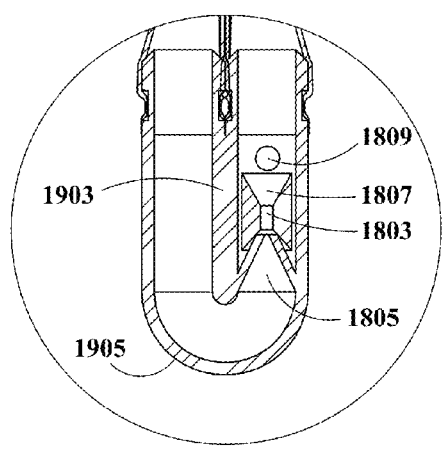
FIG. 18 illustrates an interior view of the fluid delivery tube of FIG. 17 according to one embodiment of the present invention.

Referring now to FIG. 18 an expanded view of the distal tip of the venturi feeding tube is illustrated with feeding port or valve 1809 open. Thin films form a first lumen and a second lumen. The first lumen directs fluid to a chamber and around the bend at 1905 to the mouth 1805 having a funnel to increase the velocity of the fluid as it enters the narrow throat 1803 and exit into the expansion chamber 1807 thereby creating a vacuum. Check valve 1707 (FIG. 17) is activated with the pressure drop and stomach contents are aspirated through check valve 1707. Wall 1903 separates the first chamber from the second chamber.

Figure 19:
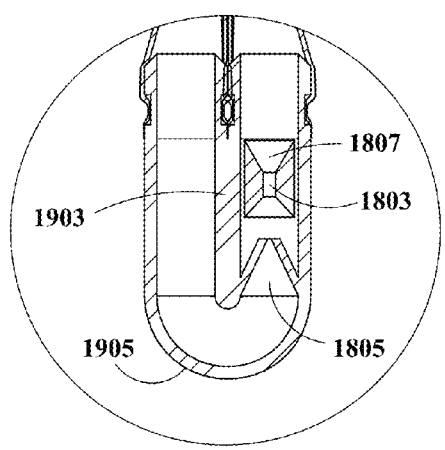
FIG. 19 illustrates a distal end interior view of the fluid delivery tube of FIG. 17 according to one embodiment of the present invention.

Referring now to FIG. 19 an expanded view of the distal tip of the venturi feeding tube is illustrated. Wall 1903 separates a first chamber from a second chamber. Within the second chamber is a mouth 1805 which is funnel shaped for increasing the velocity of the fluid as it enters the second chamber and passes into throat 1803 which leads the fluid to an expansion zone 1807 thereby creating a vacuum which may be used to aspirate fluid from the stomach through a port 1707 (FIG. 16) of the distal tip. The stomach content would be carried up the tube with the fluid as it exits the expansion zone 1807. The feeding port is closed in this view. Bend 1905 leads the fluid from the first chamber to the second chamber.

Figure 20:
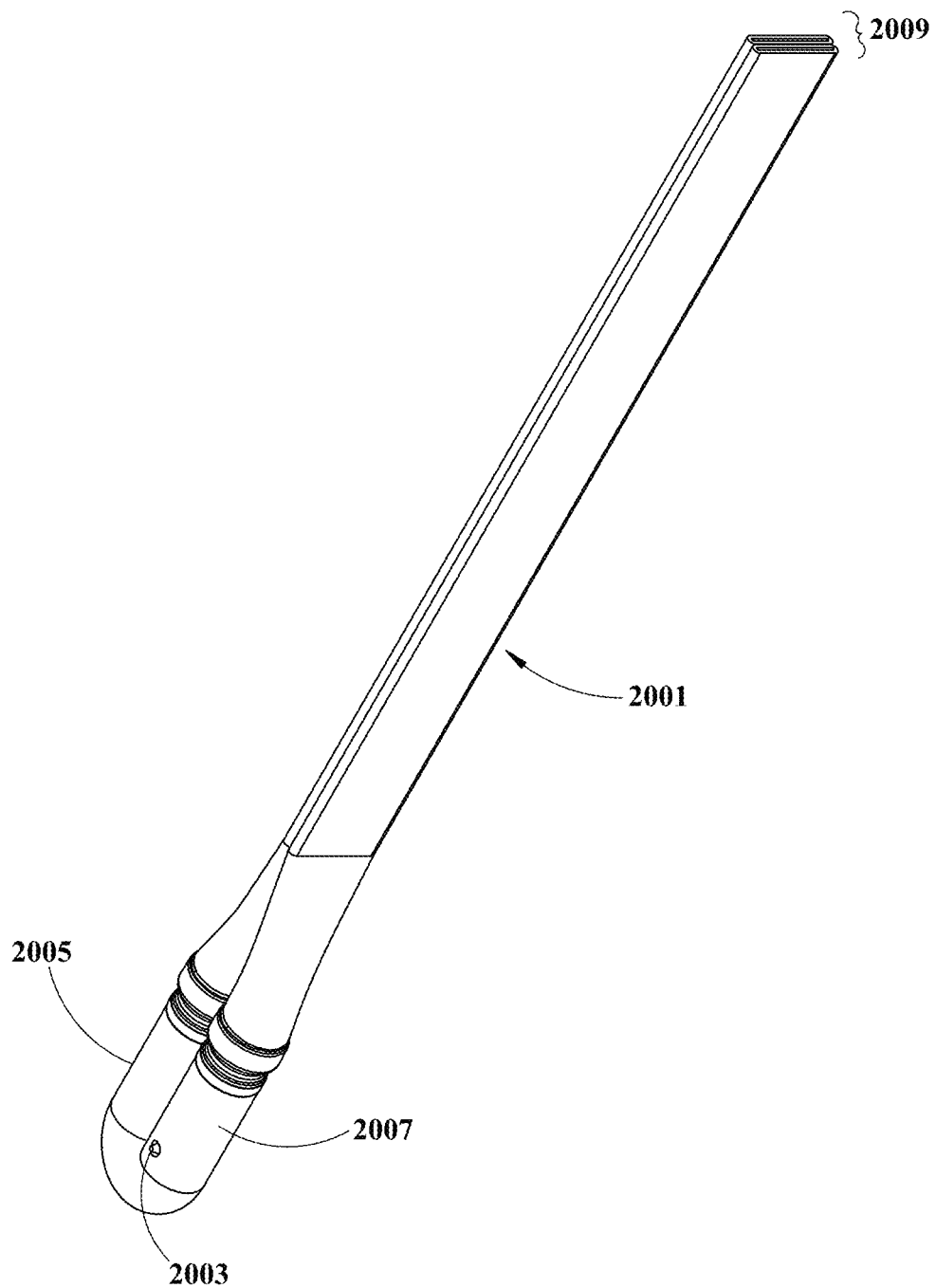
FIG. 20 illustrates a fluid delivery tube according to one embodiment of the present invention.

Referring now to FIG. 20, an embodiment of the venturi feeding tube is illustrated. Venturi tube 2001 is illustrated with two flattened lumens at end 2009. The distal tip contains a port 2003 for aspirating fluid of interest when fluid passes through the chambers 2005 and 2007 of the venturi feeding tube.

Figure 21:
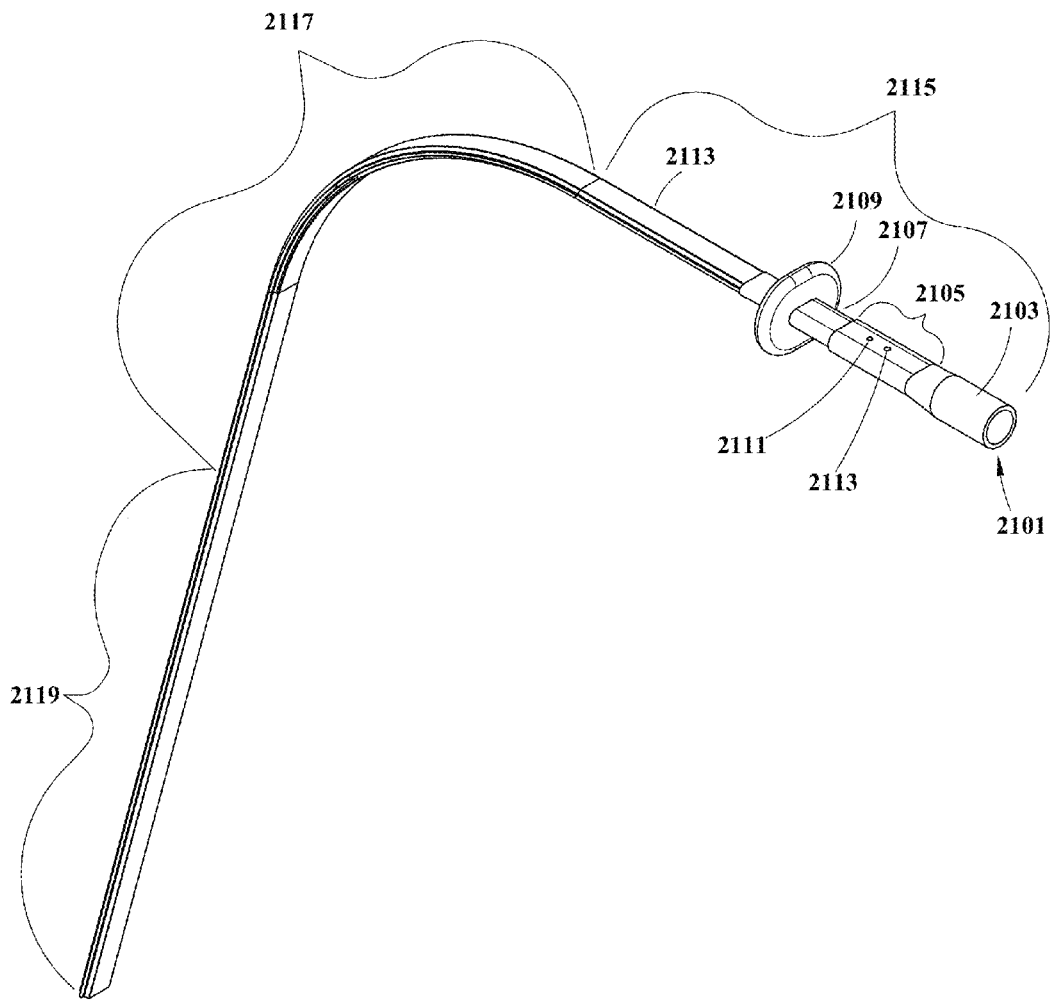
FIG. 21 illustrates a fluid delivery tube according to one embodiment of the present invention.

Referring now to FIG. 21, an embodiment of a feeding tube 2101 is illustrated. Connector 2103 allows tube 2101 to connect with a syringe (not shown) or other fluid delivery device to deliver fluid to the feeding tube 2101. The positioning member 2109 connects the connector 2103 to the flexible tube/sheath via the transitional zone 2105 having strut connector peg 2111 and 2113 located at the proximal end 2115 of the feeding tube. The distal end 2119 of the tube is connected to the proximal end 2115 through middle portion 2117 and the distal end is positioned in an opening of the mouth or nose for example and directed to the stomach. The positioning member 2109 remains outside of the body and is used to position the tube. External fluid exits the tube at the distal tip of the distal end of the tube 2119.

Referring now to FIG. 22, a feeding tube with connector 2203 at the proximal end and positioning member 2209 is connected via transitional zone 2205 which includes stationary zone 2207. Positioning member is coupled to the flexible tube 2213. Area 23 is further illustrated in FIG. 23 and area 25 is further illustrated in FIG. 25.

Referring now to FIG. 23, positioning member 2209 is shown with a longitudinal view of the interior of the tube. The interior of the tube includes struts 2303 running longitudinally in the tube.

Referring now to FIG. 24, Struts 2403 within tube 2213 is illustrated in the open state of the tube. Strut member 2405 is integral with struts 2403. Struts 2403 engages with a strut member on the opposite side of the tube.

Referring now to FIG. 25, a tube 2213 having connector 2203 and positioning member 2209 is illustrated. Area 24 and 26 are detailed in FIG. 24 and FIG. 26 respectively.

Referring now to FIG. 26, the proximal end of the tube of FIG. 25 is expanded. Connector 2203 is connected to the positioning member 2209 by a stationary zone 2613 over which sliding member 2609 moves. Sliding member 2609 includes an interface in compression that prevents fluid that enters the tube at the proximal end from leaking from the tube. Strut connector pegs 2607 and 2605 engage strut member 2611 such that the cross struts are extended as illustrated in FIG. 4 at 2403 in the open or aspiration/feeding state. The distance between the positioning member and the end of the sliding zone is represented as 3.25 mm for illustration purposes.

Referring now to FIG. 27, a feeding tube 2713 is illustrated in the closed state or non-feeding/non-aspirating state. Connector 2703 is separated from positioning member 2709 by stationary zone 2707 and sliding zone 2705. Cross sections of the tube area 28 and area 30 are illustrated in FIGS. 28 and 30.

Referring now to FIG. 28, the lateral cross section of the tube is provided illustrating the struts 2803 in the closed state with the positioning member 2709 provided for reference.

Referring now to FIG. 29, the internal portion of tube 2713 in the closed state is illustrated showing the struts collapsed which brings the sides of the walls of the tube closer together than as compared to the walls of the tube illustrated in FIG. 24 representing the tube in the open state.

Referring now to FIG. 30, the feeding tube 2713 of FIG. 27 is illustrated in a side view with connector 2703 and positioning member 2709 with area 29 and 31 expanded further in FIG. 29 and FIG. 31.

Referring now to FIG. 31, the enlarged view of the tube in FIG. 30 is illustrated. Positioning member 2709 separated from the end 3109 of the sliding member by a distance 3113, for example by about 2.91 mm, as the strut connector pegs 3107 and 3105 are collapsed down which results in the struts flattening within the tube.

Figure 32:
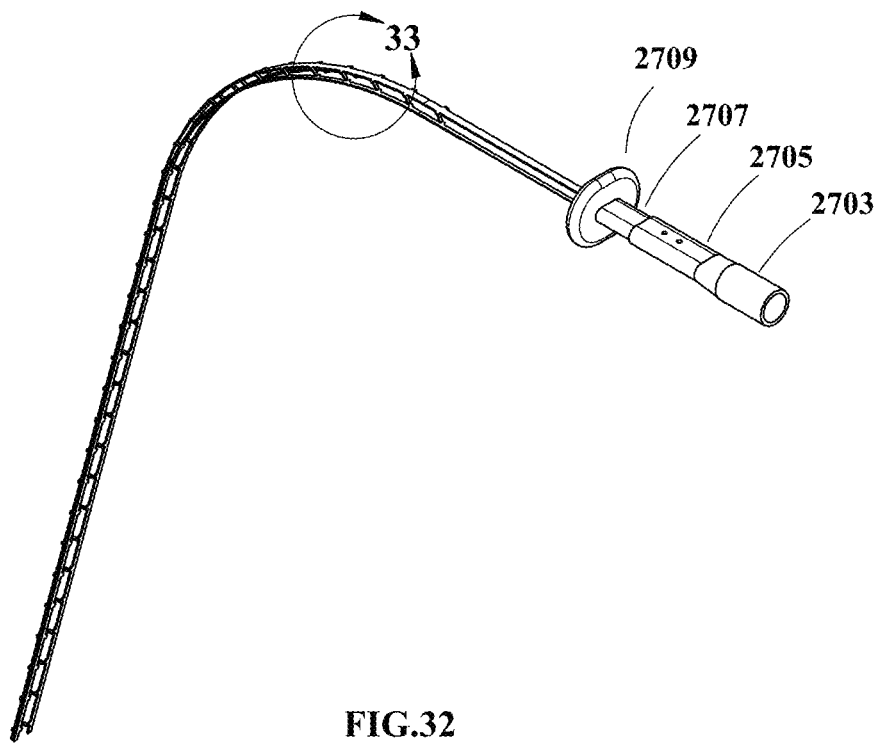
FIG. 32 illustrates a fluid delivery tube without the external tube according to one embodiment of the present invention.
Figure 33:
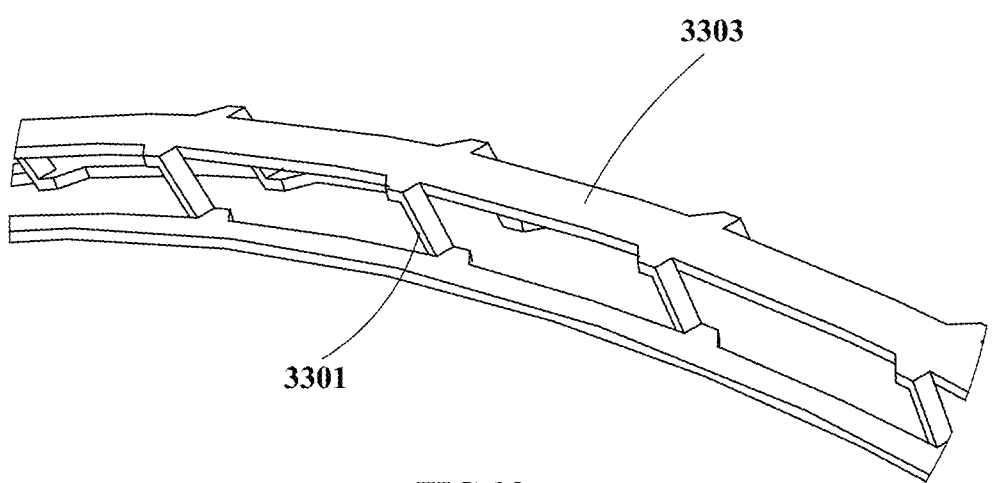
FIG. 33 illustrates a section of the fluid delivery tube of FIG. 32 according to one embodiment of the present invention.

Referring now to FIG. 32, the exterior portion of the tube is removed to show the struts engaged or extended across the interior of the tube in the open state with area 33 expanded in FIG. 33. Connector 2703 is connected to positioning member 2709 via stationary zone 2707 and sliding zone 2705.

Referring now to FIG. 33, the strut 3301 and strut member 3303 are illustrated in the open state which permits fluid to move in the tube for fluid feeding to the stomach or aspiration of the stomach content.

Figure 34:
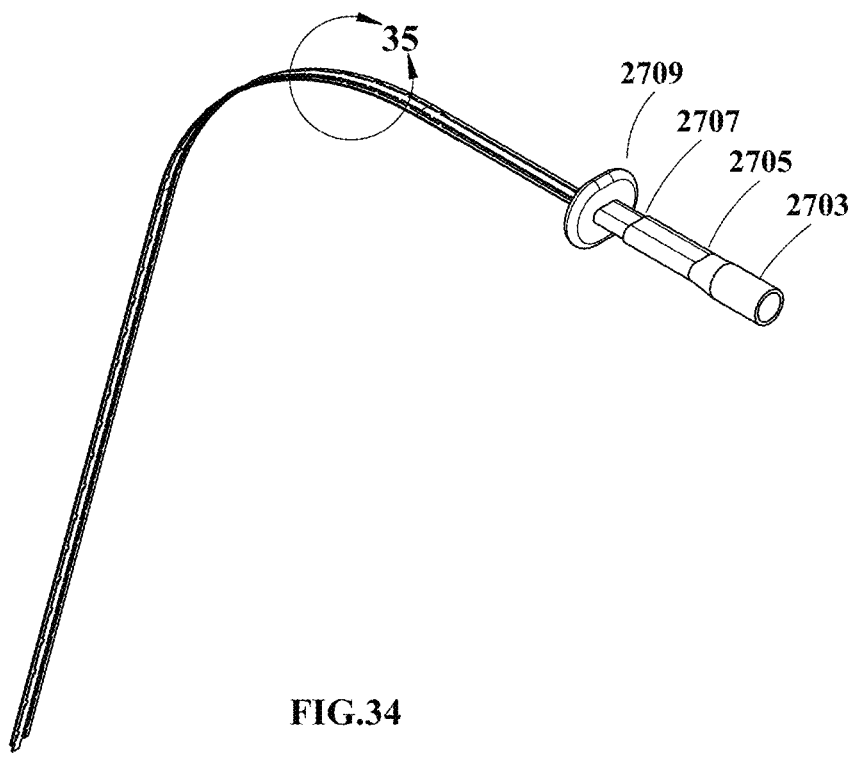
FIG. 34 illustrates a fluid delivery tube without the external tube according to one embodiment of the present invention.
Figure 35:
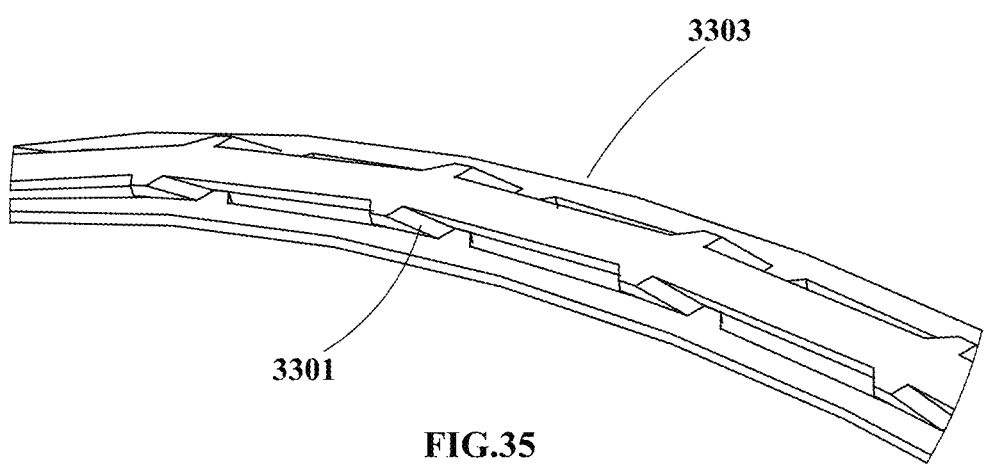
FIG. 35 illustrates a section fluid delivery tube of FIG. 34 according to one embodiment of the present invention.

Referring now to FIG. 34, the exterior portion of the feeding tube is removed to show the struts engaged in the closed state with the area 35 expanded in FIG. 35. Connector 2703 is connected to positioning member 2709 via stationary zone 2707 and sliding zone 2705.

Referring now to FIG. 35, the strut 3301 and strut member 3303 are illustrated in the closed state which inhibits or prevents fluid to move in the tube for feeding or aspiration.

Figures 36, 37:
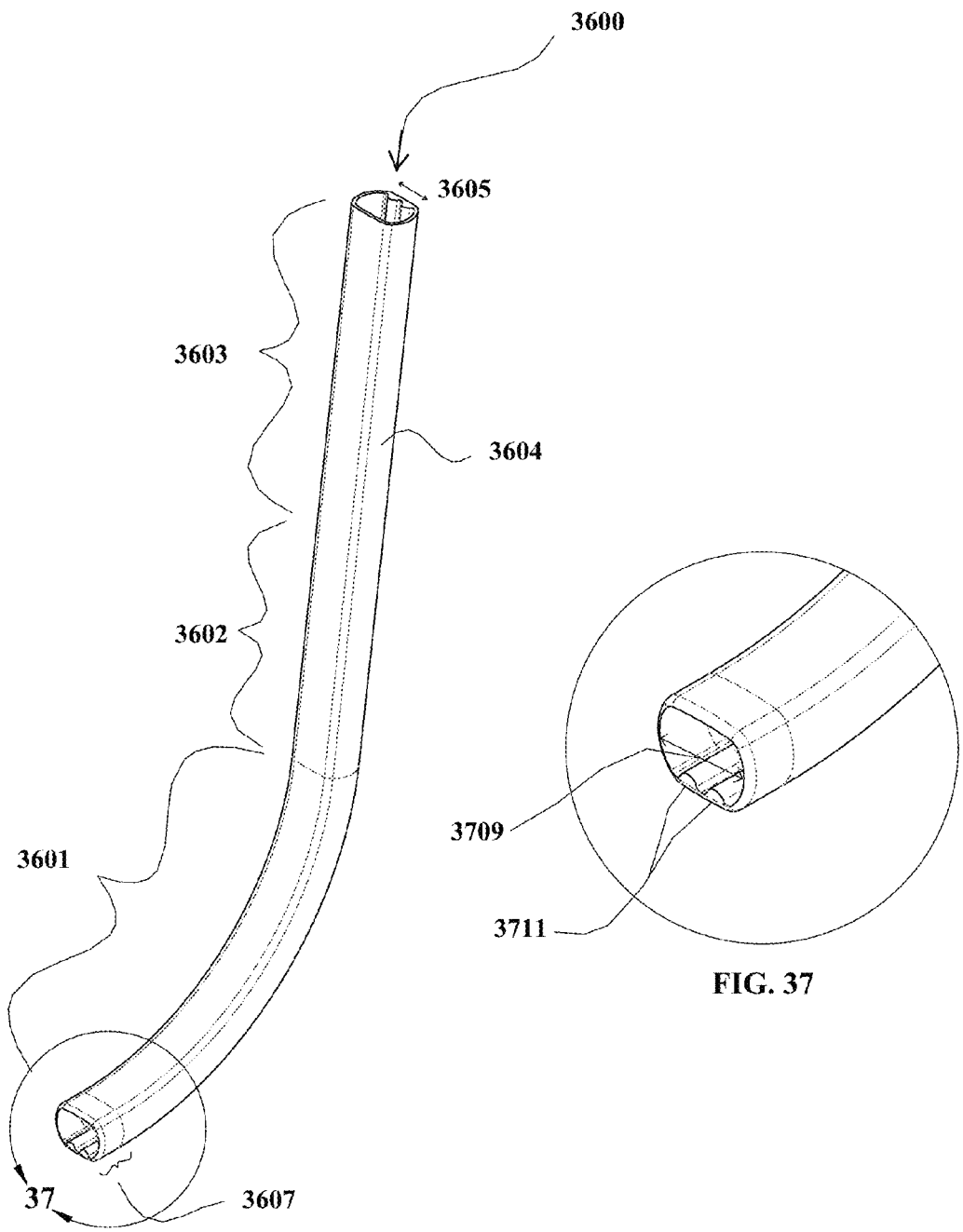
FIG. 36 illustrates a fluid delivery tube according to one embodiment of the present invention.
FIG. 37 illustrates an expanded view of the distal end of the tube of FIG. 36.

Referring now to FIG. 36, tube 3600 is illustrated having a proximal opening having a transverse axis 3605 and distal tip 3607 with area 37. The proximal portion of the tube 3603 is connected to the distal portion of the tube 3601 via the middle portion 3602. The tube is flexible and may be curved or straight. The minor axis of the tube is on the side of the tube 3604.

Referring now to FIG. 37, an enlarged view of the distal tip of the tube 3607 is illustrated having transverse axis 3709 as major axis. Ribs 3711 are formed as part of the wall along the major axis of the tube. The ribs may also be on the opposing wall of the tube (not shown). The lumen is illustrated in the open state.

Figures 38, 39:
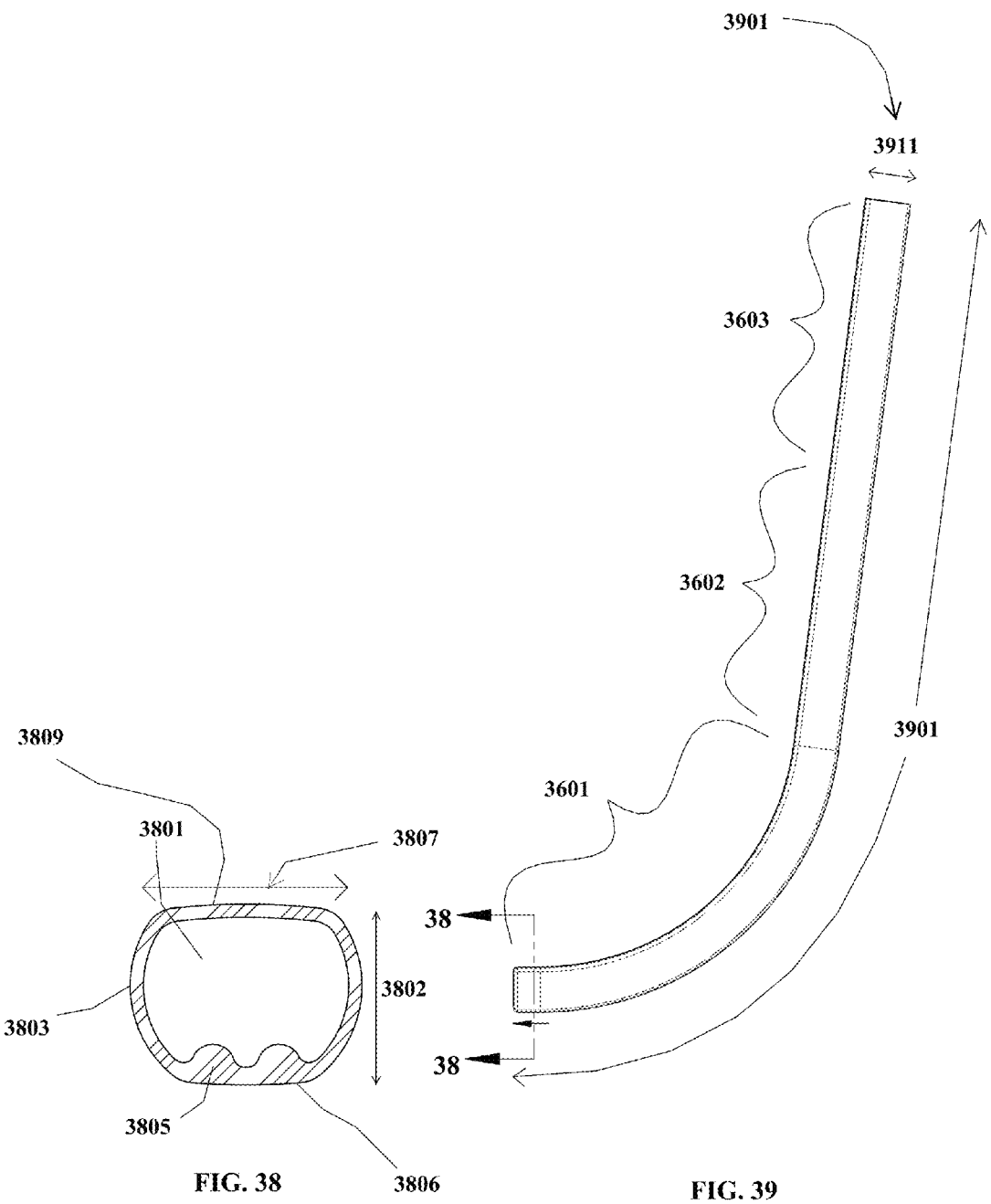
FIG. 38 illustrates an enlarged view of area 38 of the distal end of the tube of FIG. 39.
FIG. 39 illustrates a fluid delivery tube according to one embodiment of the present invention.

Referring now to FIG. 38, an end on view of the distal opening of the tube of FIG. 37 is illustrated. Lumen 3801 is formed by walls that are curved on the side 3803 and elongated along the major axis 3807 as compared to side wall 3803 along minor axis 3802. Wall 3806 includes rib 3805 and wall 3809 is without rib 3805. The rib 3805 prevents the tube from collapsing when fluid is evacuated through the tube during aspiration, for example aspiration of gastric fluid.

Referring now to FIG. 39, a side view of tube 3901 is provided as described in FIG. 36 wherein the longitudinal axis 3901 and transverse axis 3911 is illustrated. The distal end of the tube area 38 is illustrated in FIG. 38.

Figures 40, 41:
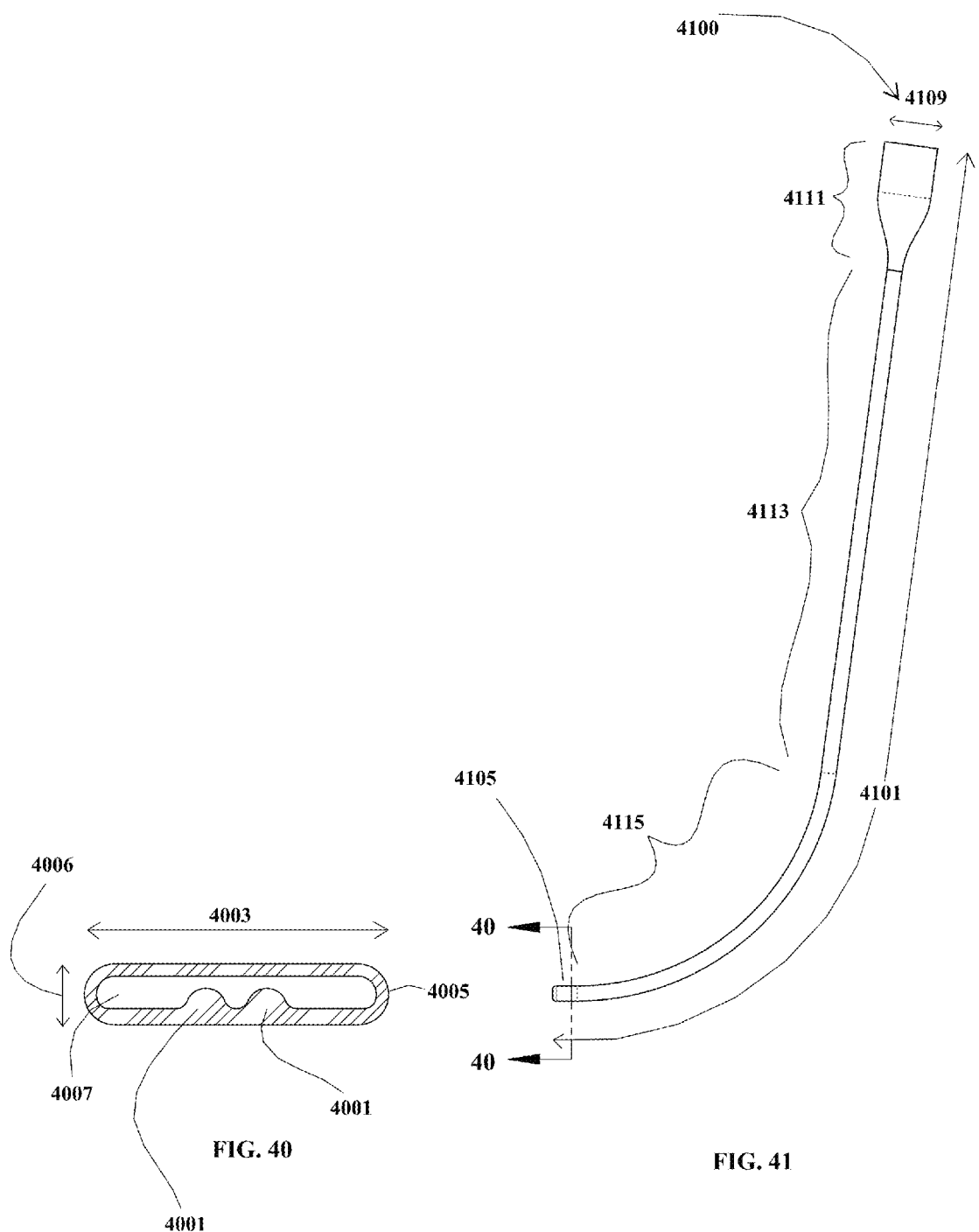
FIG. 40 illustrates an enlarged view of area 40 of the distal end of the tube of FIG. 41.
FIG. 41 illustrates a fluid delivery tube according to one embodiment of the present invention.

Referring now to FIG. 40, an end on view of the distal opening of the tube of FIG. 40 is illustrated wherein the area of the lumen 4007 is decreased when the tube is partially deformed under aspiration pressure or is compressed by environmental features such as the anatomy of the esophagus. Under aspiration conditions, the minor axis 4006 is decreased as compared to the minor axis 3802 of FIG. 38. A side along the major axis 4003 includes rib 4001 to maintain a conduit for fluid to move along the longitudinal axis of the tube when the tube is partially collapsed with side 4005 acting as a hinge to partially collapse the tube and increase the area of the side along the major axis in contact with the anatomy and thereby decrease stress on the tissue as compared to the tube in the open state of FIG. 38.

Referring now to FIG. 41, a side view of a tube 4100 with longitudinal axis 4101 and having a connector 4111 with a transverse axis 4109 at the proximal portion 4113 and a distal portion 4115 of the tube. The connector permits the tube to connect to a syringe or other means that will create suction through the tube to permit aspiration of fluid from the distal end 4105 when the distal end is placed in a fluid environment. The distal end 4105 and area 40 is illustrated in FIG. 40.

Figures 42, 43:
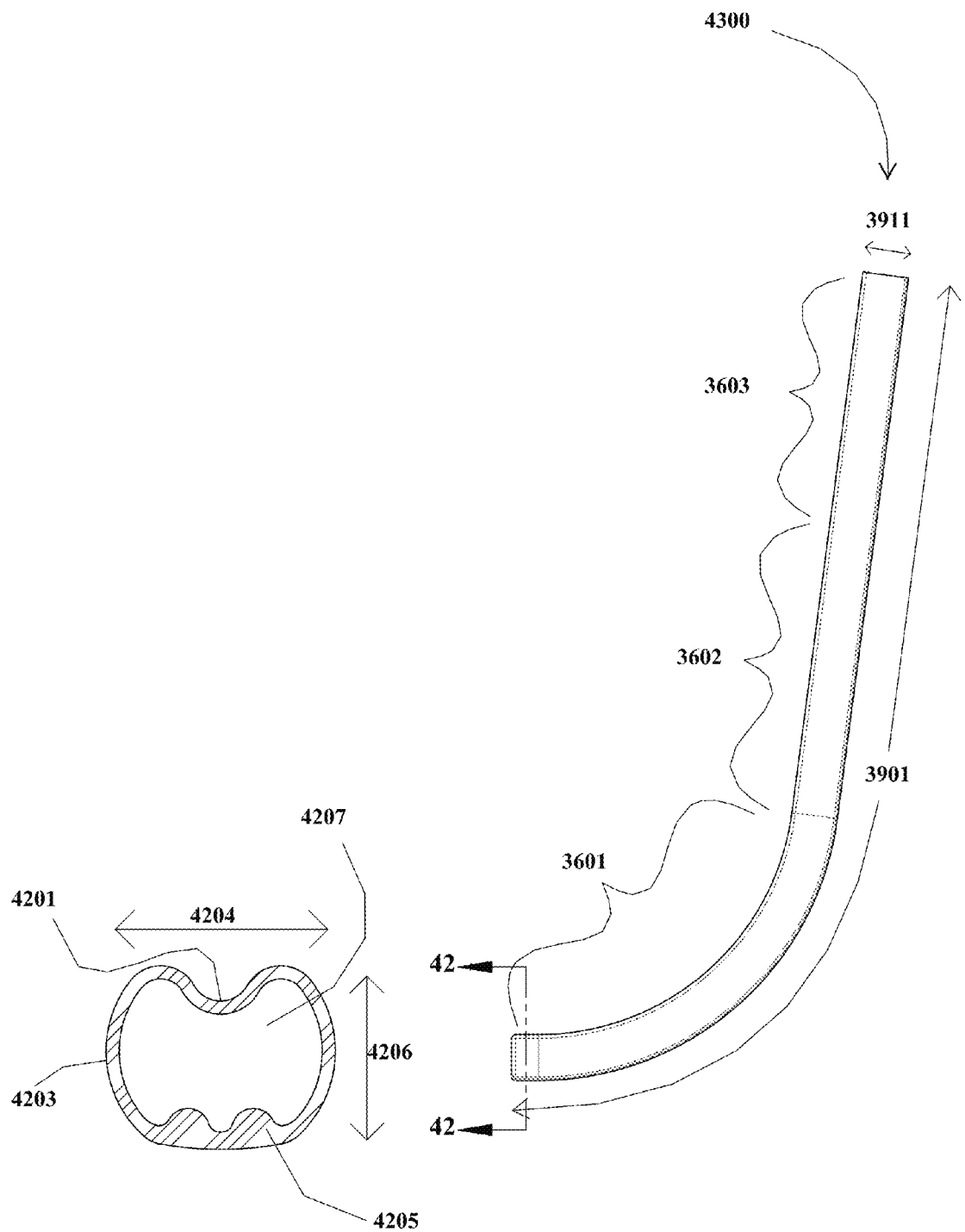
FIG. 42 illustrates an enlarged view of area 42 of the distal end of the tube of FIG. 43.
FIG. 43 illustrates a fluid delivery tube according to one embodiment of the present invention.

Referring now to FIG. 42, an alternative embodiment for the cross sectional geometry of a tube as shown and described in FIG. 43 is illustrated. In addition to a rib 4205 in the wall along the major axis 4204 there is an indentation 4201 in the wall opposite the wall with a rib. Side walls 4203 are along the minor axis 4206 and are rounded. The lumen 4207 is designed to allow fluid to pass through the channel of the tube from the proximal end to the distal end in bolus. The geometry of the tube may be deformed under suction pressure as illustrated in FIG. 44.

Referring now to FIG. 43, a side view of a tube 4300 is provided as discussed in FIG. 39 wherein area 42 is illustrated in FIG. 42.

Referring now to FIG. 44, an end on view of the distal opening of the tube 4500 is illustrated according to one embodiment of the present invention with the area of the opening decreased as compared to the area of the lumen 4401 of the tube 4207 of FIG. 42. The change in cross sectional geometry and the change in open area may result when suction is applied to the connector of the tube of FIG. 45 and the distal end of the tube is positioned in a fluid environment. The sides of the tube 4405 along the minor axis 4406 remain rounded while the sides of the tube 4407 along the major axis 4403 are longer as compared to the walls along the minor axis.

Referring now to FIG. 45, a side view of tube 4500 is provided as discussed in FIG. 41 wherein area 44 is illustrated in FIG. 44.

Figures 46, 47:
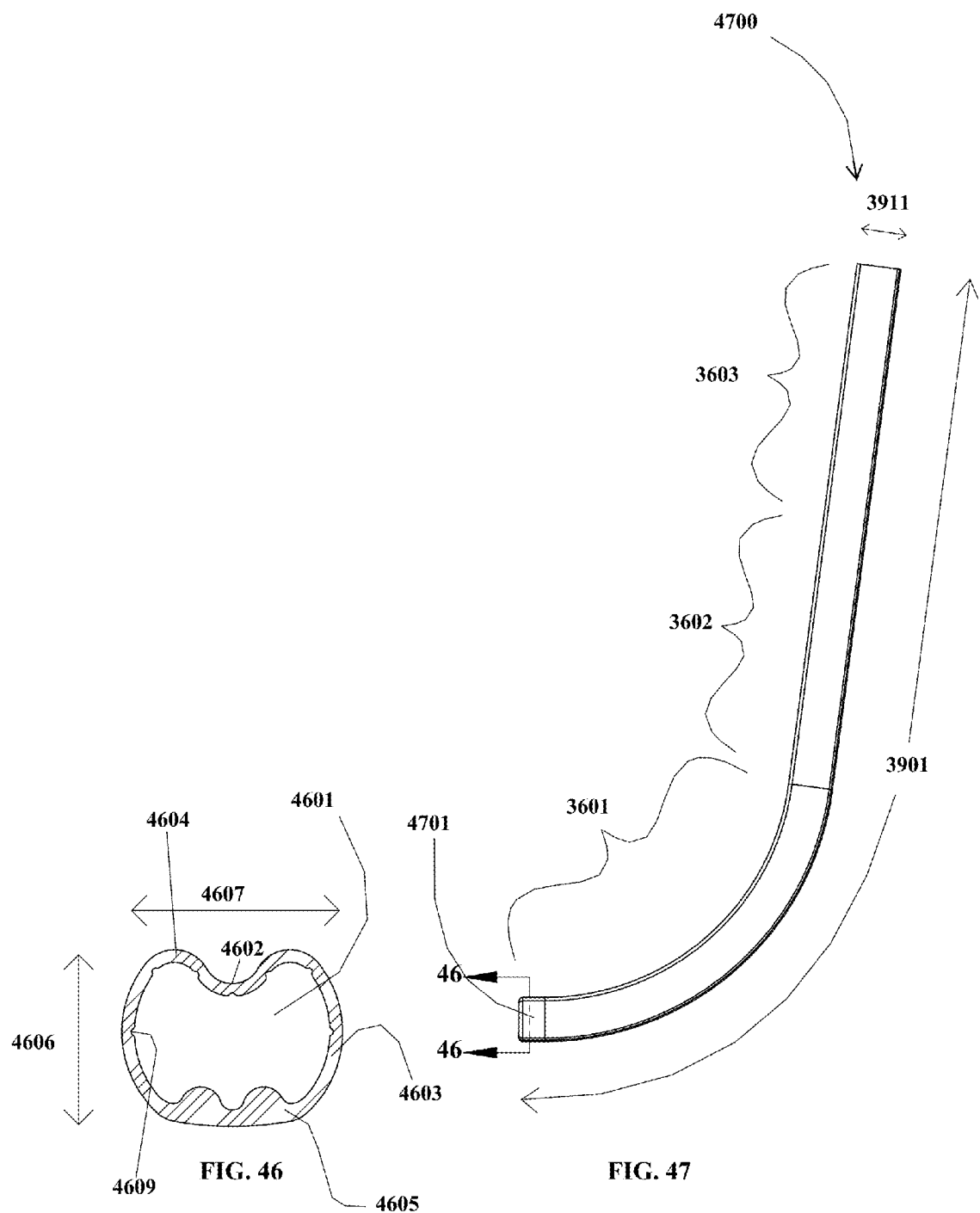
FIG. 46 illustrates an enlarged view of area 46 of the distal end of the tube of FIG. 47.
FIG. 47 illustrates a fluid delivery tube according to one embodiment of the present invention.

Referring now to FIG. 46, an end on view of the distal opening of the tube as shown and described in FIG. 39 is illustrated according to one embodiment of the present invention. The sides 4603 of the tube along the minor axis 4606 are rounded. The sides of the tube 4605 and 4604 along the major axis 4607 have an indentation 4602 at the top and a rib 4605 at the bottom and form a lumen 4601. Indentation 4602 facilitates collapse while notches 4609 act to reduce the amount of force.

Referring now to FIG. 47, a side view of tube 4700 is provided as described in FIG. 39 wherein area 46 at distal end 4701 is illustrated in FIG. 46.

Referring now to FIG. 48, an end on view of the distal opening of the tube as shown and described in FIG. 41 is illustrated according to one embodiment of the present invention. The area of the lumen 4805 is decreased as compared to the area of the lumen of the distal end of tube 4601 of FIG. 46. The change in cross sectional geometry and the change in open area may result when suction is applied to the connector 4111 of the tube of FIG. 41 and the distal end of the tube is positioned in a fluid environment. The sides of the tube 4801 along the minor axis 4802 remain rounded while the sides of the tube along the major axis 4807 are longer as compared to the walls along the minor axis. Rib 4803 in the side of the tube help maintain the tube open during aspiration.

Referring now to FIG. 49, a side view of tube 4900 is provided as described in FIG. 41 wherein area 48 of distal end 4903 is illustrated in FIG. 48.

Referring now to FIG. 50, an end on view of the distal end 5103 of tube in FIG. 51 is illustrated in area 50 according to one embodiment of the present invention. A side 5003 of the tube in the minor axis 5009 includes an inward protrusion that narrows the lumen of the tube at its center. The inward protrusion act as a hinge to facilitate the tube to collapse along its minor axis 5009. The side wall 5001 along the major axis 5007 is without a similar protrusion.

Referring now to FIG. 51, a side view of tube 5100 is provided as discussed in FIG. 39 wherein area 50 at distal end 5103 is illustrated in FIG. 50.

Referring now to FIG. 52, an end on view of the distal opening of a tube as shown and described in FIG. 53 is illustrated according to one embodiment of the present invention. The area of the opening 5201 is decreased as compared to the area of the opening of the distal end of tube 5005 of FIG. 50. The change in cross sectional geometry and the decrease in the area that is open for fluid flow may result when suction is applied to the tube of FIG. 53, at the proximal end when the distal end of the tube is positioned in a fluid environment. The sides 5205 of the tube along the minor axis 5209 protrude inward while the sides 5206 and 5203 of the tube along the major axis 5207 are less curved or have no protrusion as compared to the walls along the minor axis. The wall thickness of the tube is uniform through the longitudinal axis or along the length of the tube on any side.

Referring now to FIG. 53, a side view of tube 5300 is provided as discussed in FIG. 39 wherein area 52 at distal end 5303 is illustrated in FIG. 52.

Referring now to FIG. 54, an end on view of the distal opening of the tube as shown and described in FIG. 55 is illustrated according to one embodiment of the present invention. The tube is hexagonal in shape with one or more ribs 5507 on a side 5506 along the major axis 5509 with side 5405 along the minor axis 5511. The tube may be made of plastic that is extruded having a thicker wall on one side of the geometry, for example the side with the ribs. The thicker wall and the ribs combine to act as a spine or as a stylet to increase the rigidity of the tube for deliverability. Since the thicker wall is permanent and non-obstructive it may allow delivery of the tube without the use of a removeable stylet that is discarded after use. The thicker wall also acts as a base for the side walls which are thinner as compared to the thick wall. The side walls angle out along the minor axis. (See for example FIG. 68) The angle at the sides act as a hinge point and as a spring to allow partial collapse and to reopen the tube when the compression load has been removed. The rigidity of the thicker wall also acts as the base for the side walls. The rigidity of thicker wall insures that tube collapses preferentially along its minor axis. Collapsing the tube in its longer axis would require higher forces. The lumen 5401 formed by the walls of the tube permits an increase flow area in the lumen as compared to a tube that is round having similar cross sectional area. During bench top testing of this embodiment, a tube having the geometry of FIG. 54 that was 9 Fr OD along the major axis and 7 Fr OD along the minor axis held vertically with no bends, showed gravity flow rates that were 65% faster than that of a round tube of 8 Fr OD (present embodiment 1.72 cc/s vs round tube 8 Fr 1.04 cc/s). During in-vitro testing in simulates neo-natal anatomy, the present embodiment showed gravity flow rates that were 57% faster than that of the competitive 8 Fr OD catheter (present embodiment 1.21 cc/s vs round tube 8 Fr 0.77 cc/s).

Referring now to FIG. 55, a side view of tube 5500 is provided as described in FIG. 39 wherein area 54 at the distal end 5503 is illustrated in FIG. 54. The curvature of the side of tube 5500 is indicated by the contour lines running the length of the tube.

Referring now to FIG. 56, an end on view of one embodiment of the cross section of the tube opening 5601 is illustrated according to one embodiment of the present invention. The rib 5611 on the inner surface of wall 5606 helps to keep the tube from flattening completely on aspiration as hinge 5603 is compressed along axis 5607 and wall 5609 opposing wall 5606 comes into contact with ribs (see for example FIG. 68). The lumen area 5601 is decreased but the ribs 5611 keep portions of the lumen open. The outer cross section or OD of the tube is wider in one direction (along the major axis 5605) than as compared to the minor axis 5607 to keep a lower profile and to minimize local stress concentrations against internal anatomy. The design allows an overall cross-sectional area that is equal to an 8 Fr OD round catheter but has a 52% larger flow area in the lumen. During in-vitro testing in simulated neo-natal anatomy the aspiration flow rates for the current embodiment were 26% faster than that of the competitive 8 Fr OD round catheter (present embodiment 3.61 cc/s vs 8 Fr round tube 2.85 cc/s).

Referring now to FIG. 57, a side view of tube 5700 is provided as described in FIG. 41, wherein area 56 at the distal end 5703 is illustrated in FIG. 56. The contour of the side of tube 5700 is indicated by the lines running the length of the tube. As the tube collapses along the minor axis, the profile of the tube decreases as is illustrated by the contour lines.

Referring now to FIG. 58, an end view of one embodiment of the tube opening cross section is illustrated. A lumen 5805 is formed by sides of a tube. Ribs 5803 are formed in a side 5802 along the major axis 5807 with the side 5802 being thicker than a side 5801 along the minor axis 5809. Opposite the thicker side 5802 is a side 5806 that is shaped with a curve directed towards the lumen.

Referring now to FIG. 59, a side view of tube 5900 is provided as discussed in FIG. 39 wherein area 58 at distal end 5903 is illustrated in FIG. 58. The contour lines indicate the curvature of the tube at its side.

Referring now to FIG. 60, an end view of one embodiment of the tube opening cross section is illustrated. The area of the lumen 6003 is decreased as compared to the area of the lumen of the distal end of tube 5805 of FIG. 58. The area of the lumen may be decreased during aspiration. The side 6001 collapses preferentially along the minor axis 6007 as side 6011 comes closer to rib 6005 on side 6006 along the major axis 6009. Ribs 6005 in thicker side 6006 create rigidity of the thicker wall and acts as the base for the side walls 6001.

Referring now to FIG. 61, a side view of tube 6100 is provided as described in FIG. 41 wherein area 60 at distal end 6103 is illustrated in FIG. 60.

Referring now to FIG. 62, an end on view of one embodiment of the tube opening cross section is illustrated. The tube opening 6201 is illustrated according to one embodiment of the present invention. The rib 6205 on side 6202 helps to keep the tube from flattening completely on aspiration when side 6203 is collapsed. The outer cross section of the tube is wider in one direction (along the major axis 6209) than as compared to the minor axis 6207 to keep a lower profile and to minimize local stress concentrations against internal anatomy when the tube is used as a feeding tube for example. The notches 6204 act to reduce the force required to collapse the tube while indention 6206 acts as a flexion point to help collapse the tube along the minor axis.

Referring now to FIG. 63, a side view of tube 6300 is provided as described in FIG. 39 wherein area 62 at the distal end 6301 is illustrated in FIG. 62.

Referring now to FIG. 64, an end on view of one embodiment of the tube opening cross section is illustrated. The area of the opening 6505 is decreased as compared to the area of the opening of the distal end of tube 6201 of FIG. 62. The area of the opening may be decreased during aspiration. The side 6402 collapses preferentially along the minor axis 6507. Ribs 6403 in thicker side 6401 along major axis 6406 create rigidity of the thicker wall and acts as the base for the side walls 6402.

Referring now to FIG. 65, tube 6500 is provided as described in FIG. 41 wherein area 64 at distal end 6503 is illustrated in FIG. 64.

Figure 66:
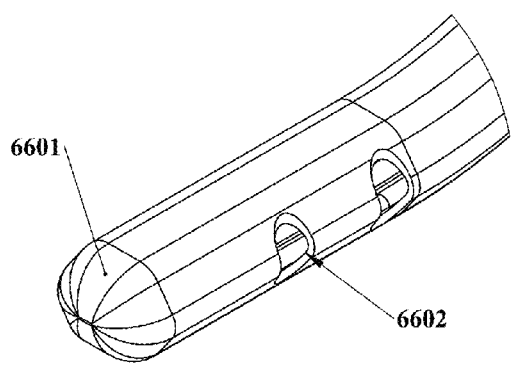
FIG. 66 illustrates a weighted tip of a fluid delivery tube with lateral ports.

Referring now to FIG. 66, a weighted end 6601 of a distal portion of a tube may include lateral ports 6602 to assist the distal end of the tube to drop into the jejunum. The distal end is illustrated in association with a gastric feeding tube in FIG. 67.

Figure 67:
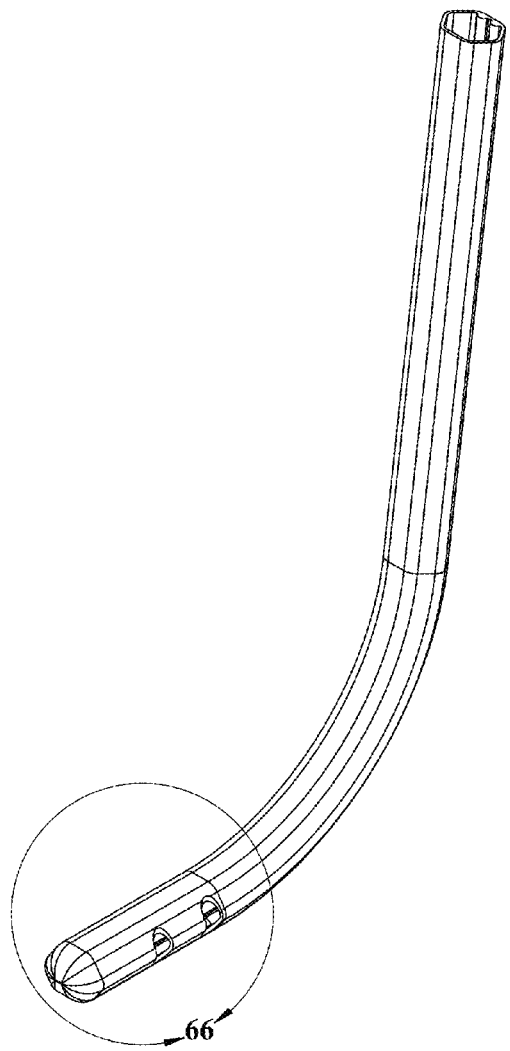
FIG. 67 illustrates a fluid delivery tube according to one embodiment of the present invention with area 66 identified at the distal end.

Referring now to FIG. 67, a gastric feeding tube according to one embodiment of the present invention is provided with area 66 illustrated in FIG. 66.

Figure 68:
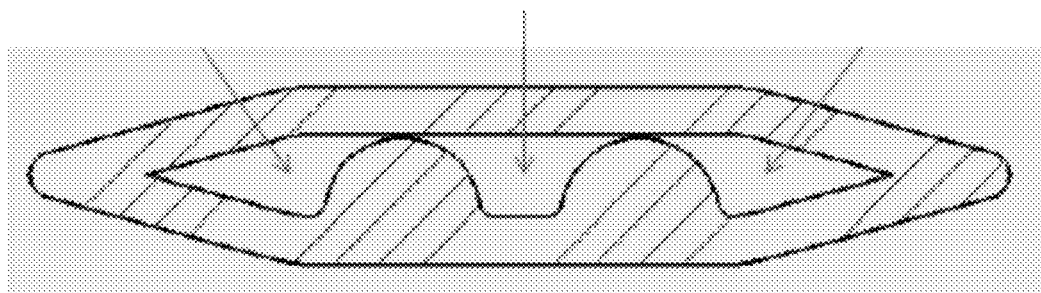
FIG. 68 illustrates a cross sectional view of a collapsed lumen with the side of the tube contacting the ribs of the tube when the tube is in a collapsed state.

Referring now to FIG. 68, a gastric feeding tube lumen in the collapsed state is illustrated wherein the ribs contact the opposing wall tube while still permitting the lumen to remain open identified by arrows.

In an embodiment described, the longitudinal axis is greater than the transverse axis. In certain applications, the longitudinal axis is intended to extend through the body passageways. The architecture of the tube and the material from which it is manufactured allows the tube to coil like a hose as the tube may be flexible and resilient. The deformability of the tube permits the internal cross sectional geometry of the tube to change during use with a tendency to resume the original fabricated shape. The tube may be produced in a relaxed state that requires force to expand the lumen area for feeding or in a relaxed state where the lumen size is reduced by force applied to the tube.

Note that in the specification and claims, "about" or "approximately" means within twenty percent (20%) of the numerical amount cited. Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A fluid delivery device of sufficient length for insertion into an esophagus of a subject via an upper airway, the fluid delivery device consisting essentially of:

a single lumen tube having a distal portion, a middle portion and a proximal portion, an inner surface and an outer surface forming a wall of the fluid delivery device, wherein the wall has a thickness and defines the single lumen of a geometry that is variable when conforming to external tissue pressure or function as it traverses the upper airway and esophagus in vivo, the single lumen having an opening at a distal end of the fluid delivery device for positioning beyond the esophagus into the stomach of the subject and an opening at the proximal end of the fluid delivery device for positioning outside of the upper airway of the subject wherein the single lumen extends longitudinally through the fluid delivery device connecting the opening at the distal end of the fluid delivery device and the opening at the proximal end of the fluid delivery device;

the single lumen circumscribes all open area within the fluid delivery device and the geometry of the single lumen is uniform through its longitudinal axis ex-vivo which has a transverse major axis and a transverse minor axis that are perpendicular and wherein a portion of the inner surface of the wall of the fluid delivery device along the transverse major axis comprises two ribs that protrude into an open area of the single lumen and thickens the portion of the inner surface of the wall of the single lumen as compared to the wall of the fluid delivery device adjacent to the two ribs and wherein the wall of the fluid delivery device along the transverse minor axis is shaped with an outward curve as compared to the wall of the fluid delivery device along the transverse major axis wherein the outward curve acts as a hinge to permit the fluid delivery device to partially collapse along the transverse minor axis of the fluid delivery device when pressure due to swallowing is applied to the outer surface of the fluid delivery device by the esophagus or upper airway passage to i) increase an area of the fluid delivery device along the major transverse axis in contact with the esophagus or upper airway passages and ii) decrease an area of the fluid delivery device along the minor transverse axis in contact with the esophagus or upper airway passages; and the two ribs prevent the fluid delivery device from fully collapsing to prevent total occlusion while allowing partial collapse of the single lumen when the fluid delivery device is in use under normal conditions.

2. The fluid delivery device of claim 1 wherein the fluid delivery device is extruded.

3. The fluid delivery device of claim 1 wherein the fluid delivery device is non-extruded.

4. The fluid delivery device of claim 1 wherein the fluid delivery device is flexible.

5. The fluid delivery device of claim 1 wherein a material from which the fluid delivery device is formed is biocompatible.

6. The fluid delivery device of claim 1 wherein the distal end of the fluid delivery device further comprises a weighted tip and lateral ports.

7. The fluid delivery device of claim 1 wherein the proximal end further comprises a connector for coupling to a feeding source.

8. The fluid delivery device of claim 7 wherein the feeding source is a pressure driven syringe filled with nutrient or gravity driven receptacle filled with nutrient.

9. The fluid delivery device of claim 1 wherein the defined geometry provides an outer cross section of the fluid delivery device that is wider along the major axis as compared to the minor axis.

10. The fluid delivery device of claim 1 wherein the wall of the fluid delivery device has increased thickness on one side of the geometry.

11. The fluid delivery device of claim 10 wherein the thickness of the wall of the fluid delivery device on one side of the lumen geometry provides stiffness without adding collapse resistance.

12. The fluid delivery device of claim 1 wherein the rib is formed of a higher durometer material as compared to the adjacent wall of the fluid delivery device.

13. The fluid delivery device of claim 1 wherein the fluid delivery device outer diameter in the transverse major axis is between 4-14 Fr and the fluid delivery device outer diameter in the transverse minor axis is between 4-14 Fr.

14. The fluid delivery device of claim 1 wherein the inner surface of the wall of the fluid delivery device is different as compared to the outer surface of the wall of the fluid delivery device.

15. A method of providing gastric feeding to a subject developing a swallowing response comprising:

inserting a fluid delivery device of claim 1 into an esophagus of the subject through an upper airway of the subject wherein a portion of the fluid delivery device at a proximal end extends outside the natural opening of the upper airway;

positioning the distal end of the fluid delivery device into the stomach; and delivering liquid nourishment to the stomach through the proximal end of the fluid delivery device located outside of the upper airway of the subject wherein a swallowing motion by the subject deforms a geometry of a lumen of the fluid delivery device as a wall of the fluid delivery device along the transverse minor axis is shaped with the outward curve which acts as a hinge to permit the fluid delivery device to partially collapse along the transverse minor axis of the fluid delivery device when pressure due to swallowing is applied to an outer surface of the fluid delivery device by the esophagus or upper airway passage and thereby increases an area of the fluid delivery device along the major transverse axis.

16. The method of claim 15 wherein the fluid delivery device may be inserted into the upper airway of the patient in the absence of a stylet or an obturator.

17. The method of claim 15 further comprising aspirating stomach content from the distal end of the fluid delivery device without totally collapsing the fluid delivery device even when the fluid delivery device is occluded by biological fluid.

18. The method of claim 15 wherein the delivering liquid nourishment is via gravity.

19. A fluid delivery device of sufficient length for insertion into an esophagus of a subject via an upper airway, the fluid delivery device consisting essentially of:
 a single lumen tube having a distal portion, a middle portion and a proximal portion, an outer surface and an inner surface forming a wall of the fluid delivery device, wherein the wall has a thickness and defines the single lumen of a geometry that is variable when conforming to external tissue pressure or function as it traverses the upper airway and esophagus in vivo, the single lumen having an opening at a distal end of the fluid delivery device for positioning beyond the esophagus of the subject and an opening at the proximal end of the fluid delivery device for positioning outside of the upper airway of the subject wherein the single lumen extends longitudinally through the fluid delivery device connecting the opening at the distal end of the fluid delivery device and the opening at the proximal end of the fluid delivery device;
the single lumen circumscribes all open area within the fluid delivery device and the geometry of the single lumen is uniform through its longitudinal axis ex-vivo which has a transverse major axis and a transverse minor axis that are perpendicular and wherein a portion of the inner surface of the wall of the fluid delivery device along the transverse major axis comprises a rib that protrudes into the single lumen and thickens the portion of the inner surface of the wall of the single lumen as compared to the wall of the fluid delivery device adjacent to the rib and wherein the wall of the fluid delivery device along the transverse minor axis is shaped with an outward curve as compared to the wall of the fluid delivery device along the transverse major axis wherein the outward curve acts as a hinge to permit the fluid delivery device to partially collapse along the transverse minor axis of the fluid delivery device when pressure due to swallowing is applied to the outer surface of the fluid delivery device by the esophagus or upper airway passage to i) increase an area of the fluid delivery device along the major transverse axis in contact with the esophagus or upper airway passages and ii) decrease an area of the fluid upper airway passages; and the rib prevents the fluid delivery device from fully collapsing to prevent total occlusion while allowing partial collapse of the single lumen when the fluid delivery device is in use under normal conditions.

* * * * *